(12) United States Patent
Nash et al.

(10) Patent No.: US 10,711,239 B2
(45) Date of Patent: Jul. 14, 2020

(54) ADIPOSE TISSUE CENTRIFUGE AND METHOD OF USE

(71) Applicant: DSM IP ASSETS, B.V., Te Heerlen (NL)

(72) Inventors: John E. Nash, Chester Springs, PA (US); William T. Fisher, Exton, PA (US); Gino Bradica, Exton, PA (US)

(73) Assignee: DSM IP ASSETS B.V., Te Heerlen (NL)

(*) Notice: Subject to any disclaimer, the term of this patent is extended or adjusted under 35 U.S.C. 154(b) by 116 days.

(21) Appl. No.: 15/949,714

(22) Filed: Apr. 10, 2018

(65) Prior Publication Data

US 2018/0230418 A1    Aug. 16, 2018

Related U.S. Application Data

(62) Division of application No. 14/610,613, filed on Jan. 30, 2015, now Pat. No. 10,125,345.
(Continued)

(51) Int. Cl.
*C12N 1/00* (2006.01)
*C12N 5/0775* (2010.01)
(Continued)

(52) U.S. Cl.
CPC ............ *C12M 47/04* (2013.01); *C12M 47/02* (2013.01); *B04B 3/00* (2013.01); *B04B 7/12* (2013.01); *C12N 5/0667* (2013.01)

(58) Field of Classification Search
CPC ...... C12M 47/04; C12M 47/02; C12M 33/10; B04B 3/00; B04B 7/12; C12N 5/0667
(Continued)

(56) References Cited

U.S. PATENT DOCUMENTS 1,921,181 A    8/1933  Fawcett
2,023,762 A    12/1935 Fawcett
(Continued)

FOREIGN PATENT DOCUMENTS

CN    2776559 Y    3/2006
DE    10314387     7/2004
(Continued)

OTHER PUBLICATIONS

Nickerson, K.W., Purification of Poly-3 Hydroxybutyrate by Density Gradient Centrifugation in Sodium Bromide, Applied and Environmental Microbiology, 1982, pp. 1208-1209., vol. 43, No. 5.

*Primary Examiner* — Walter D. Griffin
*Assistant Examiner* — Shuyi S. Liu
(74) *Attorney, Agent, or Firm* — Kevin M. Bull

(57) ABSTRACT

A centrifuge device is provided for the sizing and separation of constituents of a biologic mixture, e.g., adipose tissue. The device provides for the mechanical breaking down of the fibrous structure in the tissue by centrifugation causing the tissue to pass through a mesh element, or a sizing helix, or an extrusion element, whereupon the material is reduced to a slurry. This processed material may then be separated by centrifugation into its constituents, in order to harvest the fraction containing the multipotent cells. These multipotent cells may be utilized for various medical procedures to stimulate healing and tissue regeneration.

22 Claims, 14 Drawing Sheets

Related U.S. Application Data

(60) Provisional application No. 61/934,069, filed on Jan. 31, 2014.

(51) Int. Cl.
  *B05B 3/00* (2006.01)
  *B04B 7/12* (2006.01)
  *C12M 1/00* (2006.01)
  *B04B 3/00* (2006.01)

(58) Field of Classification Search
  USPC .............................................. 494/36, 37, 56
  See application file for complete search history.

(56) References Cited

U.S. PATENT DOCUMENTS

| | | |
|---|---|---|
| 2,136,127 A | 11/1938 | Fawcett |
| 2,596,616 A | 5/1952 | Strezynski |
| 2,822,126 A | 2/1958 | Cohn et al. |
| 2,822,315 A | 2/1958 | Cohn et al. |
| 2,873,910 A | 2/1959 | Steinacker |
| 2,906,450 A | 9/1959 | Lang et al. |
| 2,906,451 A | 9/1959 | Tullis et al. |
| 2,906,452 A | 9/1959 | Tullis |
| 2,940,662 A | 6/1960 | Applegate |
| 3,085,407 A | 4/1963 | Tomlinson |
| 3,092,582 A | 6/1963 | Lacker |
| 3,096,283 A | 7/1963 | Hein |
| 3,104,225 A | 9/1963 | Benedetto |
| 3,145,713 A | 8/1964 | Latham, Jr. |
| 3,199,775 A | 8/1965 | Drucker |
| 3,239,136 A | 3/1966 | Hein |
| 3,244,362 A | 4/1966 | Hein |
| 3,249,295 A | 5/1966 | Childs et al. |
| 3,304,990 A | 2/1967 | Ontko et al. |
| 3,332,614 A | 7/1967 | Webster et al. |
| 3,482,771 A | 12/1969 | Thylefors |
| 3,655,123 A | 4/1972 | Judson et al. |
| 3,675,846 A | 7/1972 | Drucker |
| 3,703,984 A | 11/1972 | Pruessner |
| 3,780,936 A | 12/1973 | Bush |
| 3,825,177 A | 7/1974 | Kohlstette et al. |
| 3,908,893 A | 9/1975 | Williams |
| 3,924,804 A | 12/1975 | Niemeyer |
| 3,955,755 A | 5/1976 | Breillatt, Jr. et al. |
| 3,932,691 A | 9/1976 | Schlutz |
| 4,056,225 A | 11/1977 | Hein, Jr. |
| 4,081,129 A | 3/1978 | Stroucken |
| 4,086,924 A | 5/1978 | Latham, Jr. |
| 4,111,355 A | 9/1978 | Ishimaru |
| 4,132,349 A | 1/1979 | Khoja et al. |
| 4,154,793 A | 5/1979 | Guigan |
| 4,226,669 A | 10/1980 | Vilardi |
| 4,285,464 A | 8/1981 | Latham, Jr. |
| 4,303,193 A | 12/1981 | Latham, Jr. |
| 4,304,357 A | 12/1981 | Schoendorfer |
| 4,332,350 A | 6/1982 | McClellan |
| 4,332,351 A | 6/1982 | Kellogg et al. |
| 4,341,343 A | 7/1982 | Beckman |
| 4,392,846 A | 7/1983 | Novoselac et al. |
| 4,421,503 A | 12/1983 | Latham, Jr. et al. |
| 4,425,112 A | 1/1984 | Ito |
| 4,530,691 A | 7/1985 | Brown |
| 4,629,564 A | 12/1986 | Pinato |
| 4,636,193 A | 1/1987 | Cullis |
| 4,684,361 A | 8/1987 | Feldman et al. |
| 4,700,117 A | 10/1987 | Giebeler et al. |
| 4,753,729 A | 6/1988 | Schoendorfer et al. |
| 4,776,964 A | 10/1988 | Schoendorfer et al. |
| 4,813,923 A | 3/1989 | Johansson |
| 4,816,151 A | 3/1989 | Schoendorfer et al. |
| 4,828,716 A | 5/1989 | McEwen et al. |
| 4,846,780 A | 7/1989 | Galloway et al. |
| 4,846,781 A | 7/1989 | Knelson |
| 4,854,933 A | 8/1989 | Mull |
| 4,859,333 A | 8/1989 | Panzani |
| 4,879,031 A | 11/1989 | Panzani |
| 4,889,524 A | 12/1989 | Fell |
| 4,911,833 A | 3/1990 | Schoendorfer et al. |
| 4,944,883 A | 7/1990 | Schoendorfer et al. |
| 4,959,158 A | 9/1990 | Meikrantz |
| 5,007,892 A | 4/1991 | Columbus |
| 5,032,288 A | 7/1991 | Columbus et al. |
| 5,034,135 A | 7/1991 | Fischel |
| 5,039,401 A | 8/1991 | Columbus et al. |
| 5,053,127 A | 10/1991 | Schoendorfer et al. |
| 5,076,911 A | 12/1991 | Brown et al. |
| 5,100,372 A | 3/1992 | Headley |
| 5,104,526 A | 4/1992 | Brown et al. |
| 5,147,186 A | 9/1992 | Buckholtz |
| 5,149,432 A | 9/1992 | Lavin |
| 5,188,583 A | 2/1993 | Guigan |
| 5,254,075 A | 10/1993 | Nemoto et al. |
| 5,254,076 A | 10/1993 | Chow et al. |
| 5,254,248 A | 10/1993 | Nakamura |
| 5,267,936 A | 12/1993 | Miachon |
| 5,316,540 A | 5/1994 | McMannis et al. |
| 5,316,667 A | 5/1994 | Brown et al. |
| 5,322,620 A | 6/1994 | Brown et al. |
| 5,354,256 A | 10/1994 | Knelson |
| 5,387,174 A | 2/1995 | Rochat |
| 5,387,342 A | 2/1995 | Rogers et al. |
| 5,405,308 A | 4/1995 | Headley et al. |
| 5,441,475 A | 8/1995 | Storruste et al. |
| 5,466,385 A | 11/1995 | Rogers et al. |
| 5,480,378 A | 1/1996 | Weis-Fogh et al. |
| 5,514,070 A | 5/1996 | Pages |
| 5,573,678 A | 11/1996 | Brown et al. |
| 5,585,007 A | 12/1996 | Antanavich et al. |
| 5,603,845 A | 2/1997 | Holm |
| 5,607,830 A | 3/1997 | Biesel et al. |
| 5,628,915 A | 5/1997 | Brown et al. |
| 5,632,893 A | 5/1997 | Brown et al. |
| 5,643,594 A | 7/1997 | Dorian et al. |
| 5,674,173 A | 10/1997 | Hlavinka et al. |
| 5,728,040 A | 3/1998 | Schill et al. |
| 5,733,446 A | 3/1998 | Holm |
| 5,738,784 A | 4/1998 | Holm et al. |
| 5,738,792 A | 4/1998 | Schoendorfer |
| 5,741,428 A | 4/1998 | Holm |
| 5,750,039 A | 5/1998 | Brown et al. |
| 5,776,336 A | 7/1998 | Holm |
| 5,788,662 A | 8/1998 | Antanavich et al. |
| 5,792,344 A | 8/1998 | Holm |
| 5,795,477 A | 8/1998 | Herman et al. |
| 5,795,489 A | 8/1998 | Holm |
| 5,807,492 A | 9/1998 | Brown et al. |
| 5,824,230 A | 10/1998 | Holm et al. |
| 5,830,352 A | 11/1998 | Holm |
| 5,849,178 A | 12/1998 | Holm et al. |
| 5,851,169 A | 12/1998 | Meresz et al. |
| 5,853,600 A | 12/1998 | McNeal et al. |
| 5,858,253 A | 1/1999 | Holm |
| 5,873,810 A | 2/1999 | Holm et al. |
| 5,882,289 A | 3/1999 | Sakota et al. |
| 5,935,432 A | 8/1999 | Holm |
| 5,939,319 A | 8/1999 | Hlavinka et al. |
| 5,955,026 A | 9/1999 | Holm et al. |
| 5,958,253 A | 9/1999 | Holm |
| 5,961,842 A | 10/1999 | Min et al. |
| 5,964,724 A | 10/1999 | Rivera et al. |
| 5,980,760 A | 11/1999 | Min et al. |
| 5,993,370 A | 11/1999 | Brown et al. |
| 6,007,472 A | 12/1999 | Schill et al. |
| 6,007,725 A | 12/1999 | Brown |
| 6,027,655 A | 2/2000 | Holm |
| 6,027,657 A | 2/2000 | Min et al. |
| 6,051,146 A | 4/2000 | Green et al. |
| 6,063,297 A | 5/2000 | Antanavich et al. |
| 6,099,740 A | 8/2000 | Holm et al. |
| 6,123,655 A | 9/2000 | Fell |
| 6,123,687 A | 9/2000 | Simonyi et al. |
| 6,132,598 A | 10/2000 | Hvid et al. |
| 6,139,685 A | 10/2000 | Saito |

(56) References Cited

U.S. PATENT DOCUMENTS

| | | |
|---|---|---|
| 6,214,338 B1 | 4/2001 | Antanavich et al. |
| 6,228,017 B1 | 5/2001 | Brown |
| 6,241,649 B1 | 6/2001 | Zanella et al. |
| 6,296,602 B1 | 10/2001 | Headley |
| 6,299,784 B1 | 10/2001 | Biesel |
| 6,302,836 B1 | 10/2001 | North, Jr. |
| 6,348,031 B1 | 2/2002 | Unger et al. |
| 6,387,263 B1 | 5/2002 | Bhaskar et al. |
| 6,390,964 B1 | 5/2002 | Mackel |
| 6,398,972 B1 | 6/2002 | Blasetti et al. |
| 6,416,456 B2 | 7/2002 | Zanella et al. |
| 6,475,175 B1 | 11/2002 | Rivera et al. |
| 6,511,411 B1 | 1/2003 | Brown |
| 6,530,871 B1 | 3/2003 | Mackel et al. |
| 6,544,162 B1 | 4/2003 | Van Wie et al. |
| 6,689,042 B2 | 2/2004 | Unger et al. |
| 6,716,151 B2 | 4/2004 | Panzani et al. |
| 6,716,187 B1 | 4/2004 | Jorgensen et al. |
| 6,719,901 B2 | 4/2004 | Dolecek et al. |
| 6,733,433 B1 | 5/2004 | Fell |
| 6,814,862 B2 | 11/2004 | Biesel |
| 6,835,316 B2 | 12/2004 | Dolecek |
| 6,835,353 B2 | 12/2004 | Smith et al. |
| 6,855,119 B2 | 2/2005 | Rivera et al. |
| 6,899,666 B2 | 5/2005 | Brown |
| 6,905,612 B2 | 6/2005 | Dorian et al. |
| RE38,757 E | 7/2005 | Wells et al. |
| 6,946,079 B1 | 9/2005 | Holm |
| 6,962,560 B2 | 11/2005 | Grewal |
| 6,964,646 B1 | 11/2005 | Biesel |
| 6,979,307 B2 | 12/2005 | Beretta et al. |
| 6,982,038 B2 | 1/2006 | Dolecek et al. |
| 7,001,323 B2 | 2/2006 | Panzani et al. |
| 7,029,430 B2 | 4/2006 | Hlavinka et al. |
| 7,033,501 B1 | 4/2006 | Bhaskar et al. |
| 7,037,428 B1 | 5/2006 | Robinson et al. |
| 7,060,017 B2 | 6/2006 | Collier |
| 7,060,018 B2 | 6/2006 | Skinkle et al. |
| 7,074,173 B2 | 7/2006 | Kohlstette et al. |
| 7,081,082 B2 | 7/2006 | Scholz et al. |
| 7,134,991 B2 | 11/2006 | Rivalier et al. |
| 7,156,800 B2 | 1/2007 | Panzani et al. |
| 7,179,391 B2 | 2/2007 | Leach et al. |
| 7,195,606 B2 | 3/2007 | Ballin |
| 7,204,795 B2 | 4/2007 | Himmen et al. |
| 7,223,346 B2 | 5/2007 | Dorian et al. |
| 7,252,758 B2 | 8/2007 | Dolecek et al. |
| 7,306,555 B2 | 12/2007 | Dolecek et al. |
| 7,311,849 B2 | 12/2007 | Panzani et al. |
| 7,314,441 B2 | 1/2008 | Collier |
| 7,347,932 B2 | 3/2008 | Holmes et al. |
| 7,347,948 B2 | 3/2008 | Dolecek et al. |
| 7,354,515 B2 | 4/2008 | Coull et al. |
| 7,364,657 B2 | 4/2008 | Mandrusov et al. |
| 7,374,678 B2 | 5/2008 | Leach et al. |
| 7,407,472 B2 | 8/2008 | Skinkle et al. |
| 7,413,652 B2 | 8/2008 | Dolecek et al. |
| 7,470,371 B2 | 12/2008 | Dorian et al. |
| 7,520,402 B2 | 4/2009 | Ellsworth et al. |
| 7,553,413 B2 | 6/2009 | Dorian et al. |
| 7,694,828 B2 | 4/2010 | Swift et al. |
| 7,708,152 B2 | 5/2010 | Dorian et al. |
| 7,740,760 B2 | 6/2010 | Coull et al. |
| 7,745,106 B2 | 6/2010 | Beretta et al. |
| 7,771,590 B2 | 8/2010 | Leach et al. |
| 7,780,860 B2 | 8/2010 | Higgins et al. |
| 7,789,245 B2 | 9/2010 | Westberg et al. |
| 7,803,279 B2 | 9/2010 | Coull et al. |
| 7,806,276 B2 | 10/2010 | Leach et al. |
| 7,807,461 B2 * | 10/2010 | Kang .................. C12N 5/0667 435/1.1 |
| 7,811,463 B2 | 10/2010 | Dolecek et al. |
| 7,824,559 B2 | 11/2010 | Dorian et al. |
| 7,828,709 B2 | 11/2010 | Sweat |
| 7,832,566 B2 | 11/2010 | Leach et al. |
| 7,833,185 B2 | 11/2010 | Felt et al. |
| 7,837,884 B2 | 11/2010 | Dorian et al. |
| 7,845,499 B2 | 12/2010 | Higgins et al. |
| 7,857,744 B2 | 12/2010 | Langley et al. |
| 7,866,485 B2 | 1/2011 | Dorian et al. |
| 7,867,159 B2 | 1/2011 | Dolecek et al. |
| 8,313,652 B2 | 11/2012 | Hein et al. |
| 8,317,672 B2 | 11/2012 | Nash et al. |
| 8,394,006 B2 | 3/2013 | Nash et al. |
| 8,469,871 B2 | 6/2013 | Nash et al. |
| 8,485,958 B2 | 7/2013 | Nash et al. |
| 8,556,794 B2 | 10/2013 | Nash et al. |
| 8,562,501 B2 | 10/2013 | Nash et al. |
| 8,617,042 B2 | 12/2013 | Nash et al. |
| 8,747,291 B2 | 6/2014 | Nash et al. |
| 8,758,211 B2 | 6/2014 | Nash et al. |
| 8,870,733 B2 | 10/2014 | Nash et al. |
| 8,974,362 B2 | 3/2015 | Nash et al. |
| 9,114,408 B2 | 8/2015 | Nash et al. |
| 9,358,484 B2 | 6/2016 | Tange |
| 2004/0142807 A1 | 7/2004 | Cornay et al. |
| 2005/0054506 A1 | 3/2005 | Bradley |
| 2005/0123895 A1 | 6/2005 | Freund |
| 2005/0143245 A1 | 6/2005 | Kohlstette et al. |
| 2006/0104863 A1 | 5/2006 | Bell |
| 2006/0191857 A1 | 8/2006 | Hlavinka et al. |
| 2007/0210015 A1 | 9/2007 | Egan, III |
| 2008/0011684 A1 | 1/2008 | Dorian et al. |
| 2008/0128367 A1 | 6/2008 | Rochat |
| 2011/0079044 A1 | 4/2011 | Teduka et al. |
| 2012/0129675 A1 | 5/2012 | Nash et al. |
| 2012/0156177 A1 | 6/2012 | Scarpone |
| 2012/0252650 A1 * | 10/2012 | Nash .................. B04B 1/02 494/36 |
| 2013/0012921 A1 | 1/2013 | Pustilnik et al. |
| 2013/0210601 A1 | 8/2013 | Zheng et al. |
| 2014/0021147 A1 * | 1/2014 | Leach .................. B01D 17/0217 210/781 |
| 2019/0322979 A1 | 10/2019 | Scarpone |

FOREIGN PATENT DOCUMENTS

| | | |
|---|---|---|
| EP | 0512769 | 11/1992 |
| JP | H07-313587 | 12/1995 |
| JP | H09-504985 | 5/1997 |
| JP | H09-276396 | 10/1997 |
| JP | 2001512967 | 8/2001 |
| JP | 2007236665 | 9/2007 |
| JP | 2010-115647 | 5/2010 |
| WO | WO199400169 | 1/1994 |
| WO | WO1995013142 | 5/1995 |
| WO | WO1998035758 | 8/1998 |
| WO | WO2010127278 | 11/2010 |
| WO | WO2012067658 | 5/2012 |
| WO | WO2014067658 | 5/2014 |

* cited by examiner

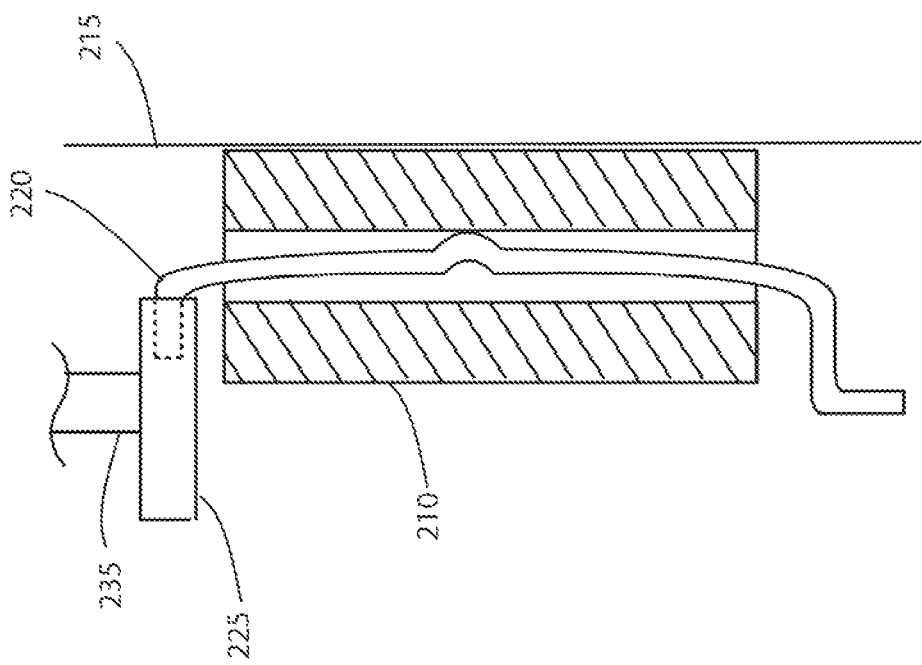
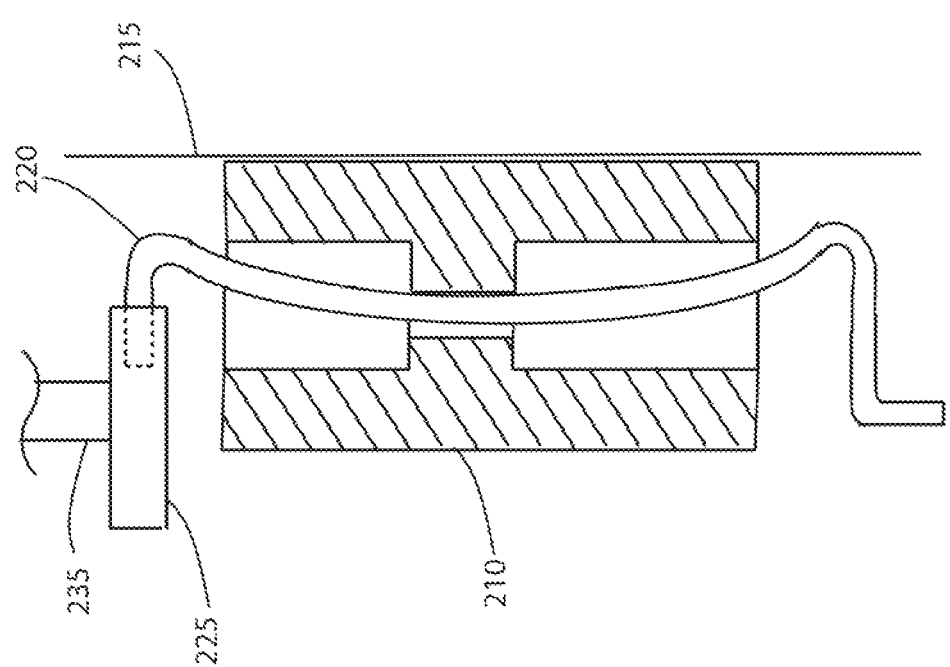

ADIPOSE TISSUE CENTRIFUGE AND METHOD OF USE

CROSS-REFERENCE TO RELATED APPLICATION

This application is a divisional application of U.S. application Ser. No. 14/610,613, filed 30 Jan. 2015, which claims the benefit of U.S. Provisional Application No. 61/934,069, filed 31 Jan. 2014, the entire contents of each of which are hereby incorporated by reference.

BACKGROUND

Multipotent cells are known to be useful in various medical procedures to assist in the healing of an affected area of a patient, for example by providing enhanced cellular regeneration of a treatment site. The multipotent cells can be sourced from various tissues of the body of a living being for use in a surgical procedure. The multipotent cells may be autologous, where the patient is the donor for the cells that are used to treat the same patient. The term "multipotent cells" includes adipose-derived stem cells, which have also been described as adipose-derived stem/stromal cells, adipose-derived adult stem cells, adipose-derived adult stromal cells, adipose-derived stromal cells, adipose stromal cells, adipose mesenchymal stem cells, lipoblast, pericyte, preadipocyte, and processed lipoaspirate cells.

It is well known that adipose tissue in the human body contains significant numbers of multipotent cells, in fact, far more multipotent cells are stored per unit volume in fat than in bone marrow. Some estimates give factors of 500:1 for the ratio of multipotent cells stored per unit volume in adipose tissue relative to those stored in bone marrow.

In order to retrieve the multipotent cells from fat, a sample of fat is retrieved from the patient by techniques known in the art, generally, for example, surgery or liposuction. It has been known to utilize enzymes, such as collagenase, or trypsin, etc., to breakdown peptide bonds in the collagen network holding the adipose tissue together, and to break down the basement membrane around the individual cells. Once this has been done, the multipotent cells may be separated out, and concentrated using centrifuge, sedimentation or filtration techniques, and the concentrate is washed to remove the enzyme (residuals) used to treat the fat sample. It is thought to be vital to remove the agents that had been added to break down the collagen network, as these enzymes are thought to cause reduced viability of the harvested cells. The washed concentrate is then available for injection back into the patient, for the purpose of accelerated repair of an injury. Unfortunately, this process to prepare a useful sample of multipotent cells, takes several hours (and in some cases up to 14 days), that makes the ad-hoc use of such a procedure difficult or impossible, required multiple processing steps, thereby increasing the potential for contamination, compromised sterility, and the process demands skilled technical knowledge.

It is previously known that in addition to preparing samples of multipotent cells isolated from adipose tissue, the multipotent cells could be isolated from a sample of bone marrow. However, in order to retrieve cells from bone marrow, the patient has to endure a very uncomfortable puncture of the marrow spaces/cavities in bone (e.g., the iliac crest) before bone marrow aspirate (BMA) is drawn. The BMA sample is then spun down in a centrifuge to gain a cellular concentrate that can then be injected into the patient for the repair of some injury. Although the timing of this procedure permits the ad-hoc use in an operatory, the concentrate obtained may have an insufficient dose level for some applications without adopting a culturing method to increase the concentration. The procedure utilizing BMA may be competitive to procedures using multipotent cells from fat, however, the harvesting of tissue for BMA procedures has the disadvantage of requiring a painful access procedure.

Accordingly, a need exists for a rapid multipotent cell collection, isolation and concentration apparatus and procedure that enables the ad-hoc use of harvested cells in a surgical procedure, where the harvested cells can be prepared in a short timeframe (less than 5 minutes), and capable of being performed following a simple protocol with easy steps that do not require extensive technical training. The subject invention addresses that need (and others) by providing a compact, sterile, self-contained, easy-to-use centrifugal separation unit to provide quick and reliable multipotent cell isolation from collected or harvested fatty tissue and methods for quickly and reliably isolating multipotent cells from collected or harvested fatty tissue. The fatty tissue can be collected or harvested by any means known in the art, including, but not limited to, liposuction and surgically harvested fat. In the case of adipose tissue, the biologic mixture consists of the fatty and fibrous tissue, plus a portion of the tumescent fluids used to stabilize the fat for extraction (e.g., saline, epinephrine, lidocaine, etc.), with the multipotent cells residing in the fatty and fibrous tissue. To isolate the multipotent cells for harvesting, the device mechanically breaks down the collagen structure, and separates its fractions by specific gravity, in order to isolate the fraction containing the multipotent cells for collection and use in various types of procedures, be they diagnostic, therapeutic, or surgical.

With regard to fat processing for reimplantation, one may alternatively obtain a sample of harvested fat to be utilized surgically, in a manner that does not require separating out the multipotent stem cells from the tissue structure, as described immediately above. Fat transfer, for example, also referred to as autologous fat grafting, involves the removal and re-implantation of a patient's adipose tissue. The adipose material is typically removed from areas of the body like the abdomen, thighs, or buttocks. Depending on the extraction technique (e.g., surgical removal, liposuction, etc.), it may be necessary to remove the certain portions of the harvested sample (e.g., tumescent solution) from the tissue extract. It may further be necessary, depending on the techniques used to harvest the sample, to size the tissue, in order to create a homogenous product and present a material with appropriate particulate sizes for the purpose intended. Sizing of the tissue is desirable in many clinical applications where there is limited access for re-implanting the sample. For example, where there are aesthetic concerns (e.g., facial cosmetic procedures), in order to minimize scarring from incisions, the procedure may be performed by injecting the material via a small diameter needle. When used as a facial filler, fat grafting can improve the creased and sunken areas of the face, and add fullness to the lips and cheeks. Fat grafting is also commonly used in breast and buttocks augmentation, usually in place of implants.

Current fat grafting is performed by harvesting the adipose material, using a variety of techniques and surgical tools. Consequently, the product that is harvested may be quite different in cell viability, texture (e.g., particle size) and composition (e.g., fatty tissue, blood, tumescent solution, oil, saline, water), as a result of the technique utilized for harvesting. This results in variability in the material that may beneficially be accounted for during the processing of the fat sample prior to re-implantation. Furthermore, the preparation techniques and instruments applied to the fat sample for re-implantation may also vary, potentially resulting in a product prepared for re-implanting that may be sized to a particle size that is too small for the intended use of the material, resulting lower cellular viability attributable to the excessive processing, increasing the potential for washout of the implanted material and/or volume loss in the implanted site. Alternatively, a sample that is sized to particle size that is too large for the intended use may result in challenges upon implantation, such as uneven texture, blockages of the narrow gauge needles utilized for re-implantation, and difficulty in the revascularization of the large particle size graft which may negatively affect viability.

What is needed is a device that is able to size the material to a useful consistency, and is able to provide a reliable composition of the material for implantation, regardless of the original collection technique, in order to avoid the above mentioned problems.

What is needed further needed is a unitary device that can quickly process, in a sterile, closed system, the fat harvested for fat grafting, into a homogenous material, having a reliably uniform particle size. The ideal device would consistently size the material in a manner that is independent of the manner of initial harvesting of the fat sample. Additionally, what is needed is a device capable of removing at least a substantial portion of unwanted components from the harvested sample, and preserving the components to be implanted, such as by removing from the sample one or more of: blood, water, saline, oil, tumescent solution. Additionally, the ideal device would minimize the potential for damage to the cellular components and tissue structure within the sample, in order to maximize the viability of cells to be implanted.

SUMMARY OF THE INVENTION

In accordance with an aspect of this invention, a centrifuge for processing a biologic mixture, e.g., adipose tissue, and selectively concentrating its constituents is provided. Those constituents have differing specific gravities and are stratifiable in a centrifugal field produced by the centrifuge. The centrifuge comprises a processing assembly and a rotation source. The processing assembly comprises an inner chamber, an outer chamber, at least one cutting element and an annular screen. The inner chamber is arranged to contain a biologic mixture, and has a central longitudinal axis about which the inner chamber is arranged to be rotated and comprises a conical member, a base and at least one extrusion hole at a first location along the central longitudinal axis and extending radially through the inner chamber. The outer chamber is arranged to receive a biologic mixture from the inner chamber and is arranged coaxially upon the central longitudinal axis of the inner chamber and around the inner chamber. The outer chamber is arranged to rotate about the central longitudinal axis and comprises an outer chamber wall and a dish. The at least one cutting element is positioned between a portion of the inner chamber and the outer chamber and is arranged to remain stationary relative to the rotation of the inner and outer chambers. The annular screen is positioned between the cutting element and the outer chamber. The screen provides a series of openings therein and is arranged to rotate about the central longitudinal axis. The rotation source is coupled to the inner and outer chambers.

In accordance with another aspect of this invention a centrifuge for selectively concentrating at least one constituent of a biologic mixture, e.g., adipose tissue, is provided. The constituents have differing specific gravities and are stratifiable in a centrifugal field produced by the centrifuge. The centrifuge comprises an inner chamber arranged to receive the biologic mixture and has a central longitudinal axis about which the inner chamber is arranged to be rotated. The inner chamber comprises a sidewall having a tapered inner surface, a base, an annular screen, and optionally, a trap and at least one roller. If present, the trap is located in the inner chamber adjacent the inner surface of the sidewall. The annular screen has an inner surface and is located at a first radial distance from the central longitudinal axis. The annular screen projects away from the base. The at least one roller is arranged to effectively roll around the inner surface of the screen to propel at least a portion of the biologic mixture through the screen and away from the central longitudinal axis and towards the tapered sidewall.

In accordance with another aspect of this invention a method of for processing a biologic mixture, e.g., adipose tissue, and selectively concentrating constituents of the biologic mixture is provided. The constituents have differing specific gravities and are stratifiable in a centrifugal field. The method basically entails providing the biologic mixture into an inner chamber of a centrifuge. The inner chamber has at least one extrusion hole. The centrifuge additionally comprises an outer chamber disposed about the inner chamber. The inner chamber is rotated about an axis to extrude a portion of the biologic mixture through the extrusion hole. Portions of the biologic mixture from the extrusion hole are cut off to produce a morselized biologic mixture. The morselized biologic mixture is introduced into the outer chamber and the outer chamber is rotated about an axis to cause the morselized biologic mixture to stratify in the outer chamber into at least two concentric stratified constituent layers (e.g., one of which being multipotent cells).

In accordance with another aspect of this invention a method of for processing a biologic mixture, e.g., adipose tissue, and selectively concentrating constituents of the biologic mixture is provided. The constituents have differing specific gravities and are stratifiable in a centrifugal field. The method basically entails providing the biologic mixture into an inner chamber of a centrifuge, and while rotating the chamber about a longitudinal axis, causing at least a portion of the biologic mixture in the chamber to be sized by passing through a rotating screen element having small openings therein. Continued rotation of the chamber will cause the sized biologic mixture to stratify in the outer chamber into at least two concentric stratified constituent layers.

In the various exemplary embodiments described herein, there is provided a motor or drive unit, which serves as a rotation source for the processing unit. Preferably, the motor unit is separable from the processing unit, such that the motor unit may be reused, while the processing unit is preferably a single-use component, though it is contemplated that the processing unit may be cleaned and sterilized, such that it may be reused as well. The processing unit is an assembly, made up of an inner chamber and an outer chamber. The inner chamber is constructed of a sidewall and a base. The sidewall has a tapered inner surface. The inner chamber includes one or more extrusion holes extending radially through the sidewall of the inner chamber at its widest diameter. The inner and outer chambers are arranged to rotate and be driven by the rotation source.

In some of the exemplary embodiments described herein, there may be a static element positioned between the rotating inner and outer chambers. The static element has at least one cutting element which, in cooperation with the one or more extrusion holes of the rotating inner chamber, serves to morselize the tissue into smaller fragments. In these embodiments, as the inner chamber is rotated, the centrifugal force drives the biologic mixture through an extrusion hole, and upon encountering the cutting element of the static element, the ejected material is cut into smaller units, becoming morselized. Furthermore, some of these embodiments may also have a screen arranged between the static element and the outer chamber. As the morselized tissue encounters the screen, continued centrifugal force will urge the material through the screen, thereby capturing the fibrous material on the screen, and passing the non-fibrous material to the outer chamber. This screen may also serve to further reduce the particle size of the material as it passes through the openings.

Once the morselized material is in the outer rotating chamber, the larger diameter of the outer chamber will subject the morselized material to greater centrifugal forces, relative to those in the inner chamber, if the rotational speed is kept constant. Alternatively, should one want to maintain the level of G forces at a constant level, the rate of rotation could be reduced once the majority of the tissue material is in the outer chamber. While in the rotating outer chamber, the morselized material will stratify into annular layers, based upon the specific gravity of the constituents of the biologic mixture. It is understood that the rotation rate may be varied during the processing and separation, such as rotating at a first velocity while the material is within the inner chamber and while passing through the extrusion hole and past the static cutting element; then rotating at a second velocity while the material is within the outer chamber in order to achieve the separation of the constituents by their specific gravities.

In various other exemplary embodiments of the device, the processing unit is an inner chamber, with an internal screen element. The biologic mixture is added to the interior of the chamber, and as the device is rotated, the material will encounter the screen. Continued rotation will urge the material through the screen, which will morselize the material as it passes through the opening. Furthermore, the screen may capture much of the fibrous elements in the material, and passing the non-fibrous elements through the openings to the chamber wall, where the morselized material can separate by specific gravity. In some of these exemplary embodiments having a screen, an optional roller may be provided to further urge the material through the screen. In such an embodiment, as the material spreads out along the inside surface of the rotating screen, the material will encounter a roller arranged parallel to the screen, essentially rolling in place against the rotating screen, thus the material will be pushed through the openings in the screen as the material encounters the roller.

In various exemplary embodiments described herein, the chamber wall, and the base of the inner chamber may form a trap in order to capture the highest density fraction of the fluid in the chamber, as the constituents are separated by specific gravity due to the rotation of the centrifuge about the central longitudinal axis. This trap is arranged so that upon cessation of rotation of the chambers of the centrifuge device, the effects of gravity overcome the centrifugal force acting on the material within the device, the constituent fraction within the trap will remain within the trap, and not mix with the remaining material within the chamber, as that lighter fraction pools due to gravity in the center of the inner chamber. The fraction remaining within the trap may then be harvested by various techniques and applied to tissue to aid in repair.

Alternatively, in other exemplary embodiments where the cells are being retained within the native structure of the tissue material, a substantial portion of the liquids will be removed from the tissue and accumulate in the trap, however, a substantial portion of the desired cells will remain within the inner chamber in fat for collection and use in surgical procedures where a scaffold material may be useful.

In accordance with another aspect of this invention, a centrifuge for processing a biologic mixture, e.g., adipose tissue, by sizing the material, and selectively concentrating its constituents is provided. The centrifuge comprises a processing assembly, and a rotation source. The processing assembly comprises a rotatable chamber arranged to receive the biologic mixture, and a rotatable tube housing a rotatable sizing helix therein. The rotatable chamber comprises a sidewall with a tapered inner surface, and optionally, a trap. The rotatable chamber and the rotatable sizing helix are arranged to be driven by the rotation source. As the sample material is introduced into the chamber through the delivery tube, the rotation of the helix will reduce the particle size of the material. The chamber may be rotated about its longitudinal axis to separate the components of the biologic mixture by specific gravity.

The isolated fraction containing the multipotent cells may be harvested and stored for later use, or immediately directed into a patient for treatment in a medical procedure.

BRIEF DESCRIPTION OF THE DRAWINGS

FIGS. 6A and 6B are respective enlarged cross sectional views of the screen and suspended roller elements constructed in accordance with this invention.

DETAILED DESCRIPTION

Figure 1:
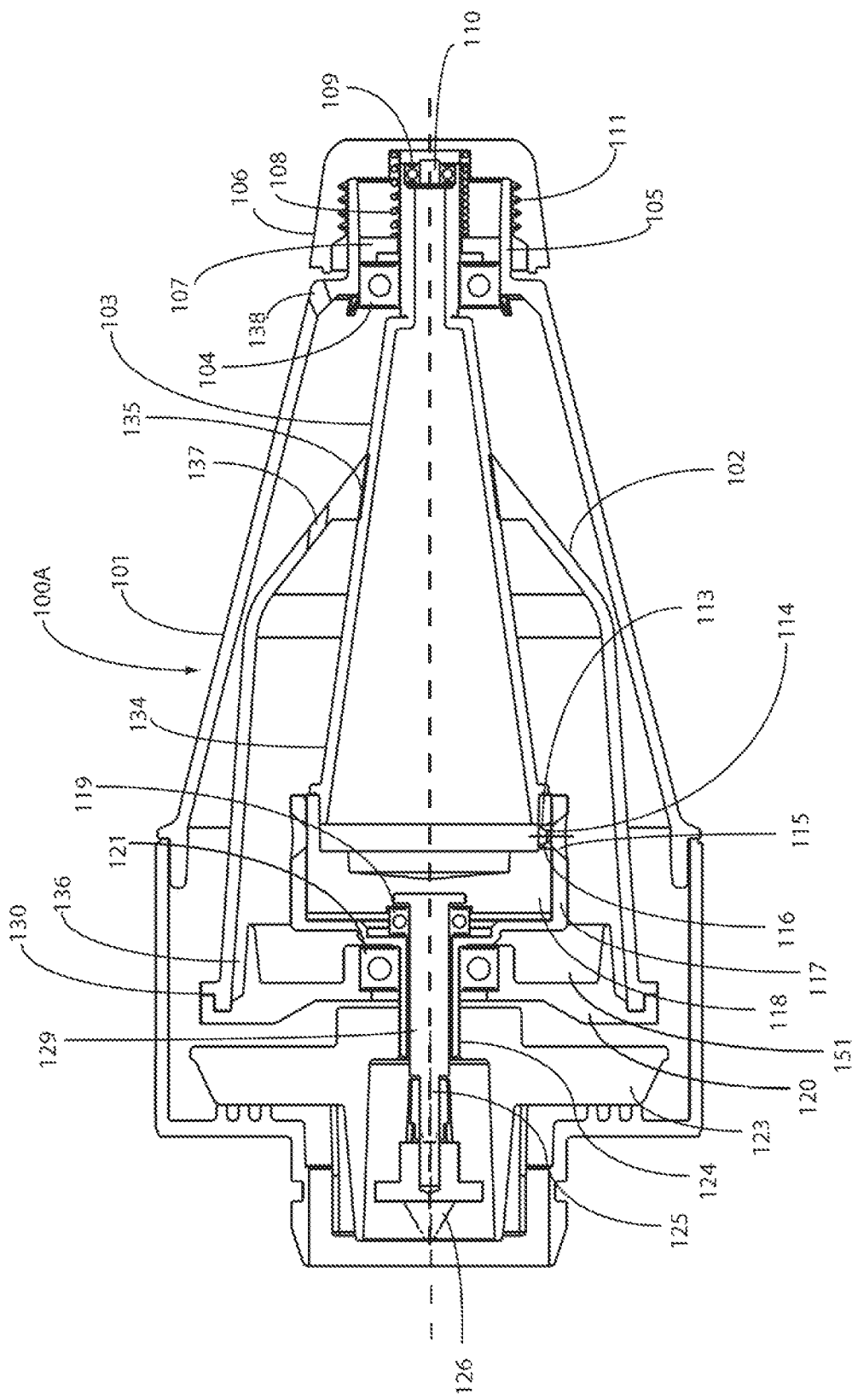
FIG. 1 is a cross sectional views of one portion, i.e., a processing unit comprising an inner and outer chamber, of one exemplary embodiment of a centrifuge device constructed in accordance with this invention and arranged for morselization and separation of tissue.

Referring now to the various figures of the drawing, wherein like reference characters refer to like parts, there is shown in FIG. 1 one exemplary embodiment of a portion of a centrifuge constructed in accordance with this invention. The centrifuge basically comprises a processing unit or assembly (one exemplary embodiment 100A of which is shown in FIG. 1) and a base or drive unit 20 (shown in FIG. 2). The details of the construction and operation of the processing unit 100A and the base unit 20 will be described later. In addition, the details of other exemplary processing units will also be described later. In some of the exemplary embodiments described herein, the processing unit includes a rotatable outer chamber 102 and a rotatable inner chamber 103. The inner chamber is arranged to receive a biologic mixture, such as fibrous tissue, e.g., adipose (fatty) tissue, and to be rotated with respect to a stationary cutting element (to be described later) to extrude the tissue past the cutting element where it is broken down mechanically and from whence the broken down tissue is introduced into the outer chamber. The outer chamber is also arranged to be rotated to effect the separation of the broken-down tissue components by the centrifugal force produced by the rotation of that chamber.

While it has previously been known that the fibrous network in fatty tissue can be broken down by using enzymatic agents, it is currently sought to break down the fibrous network in the harvested adipose tissue by using solely mechanical means, so as to allow, in some embodiments, the release of the multipotent cells contained within the fibrous network. This mechanical breaking down of the fibrous network should avoid the need to wash out an enzymatic agent, and may be accomplished using the various embodiments of the centrifuge devices described herein. For clarity, the term morselized is used to describe the process of mechanically reducing a tissue having an initial fragment size into fragments of a smaller size by the centrifuges of this invention, also known as sizing of the tissue. The terms "morselize" and "size" are used interchangeable herein.

Figure 2:
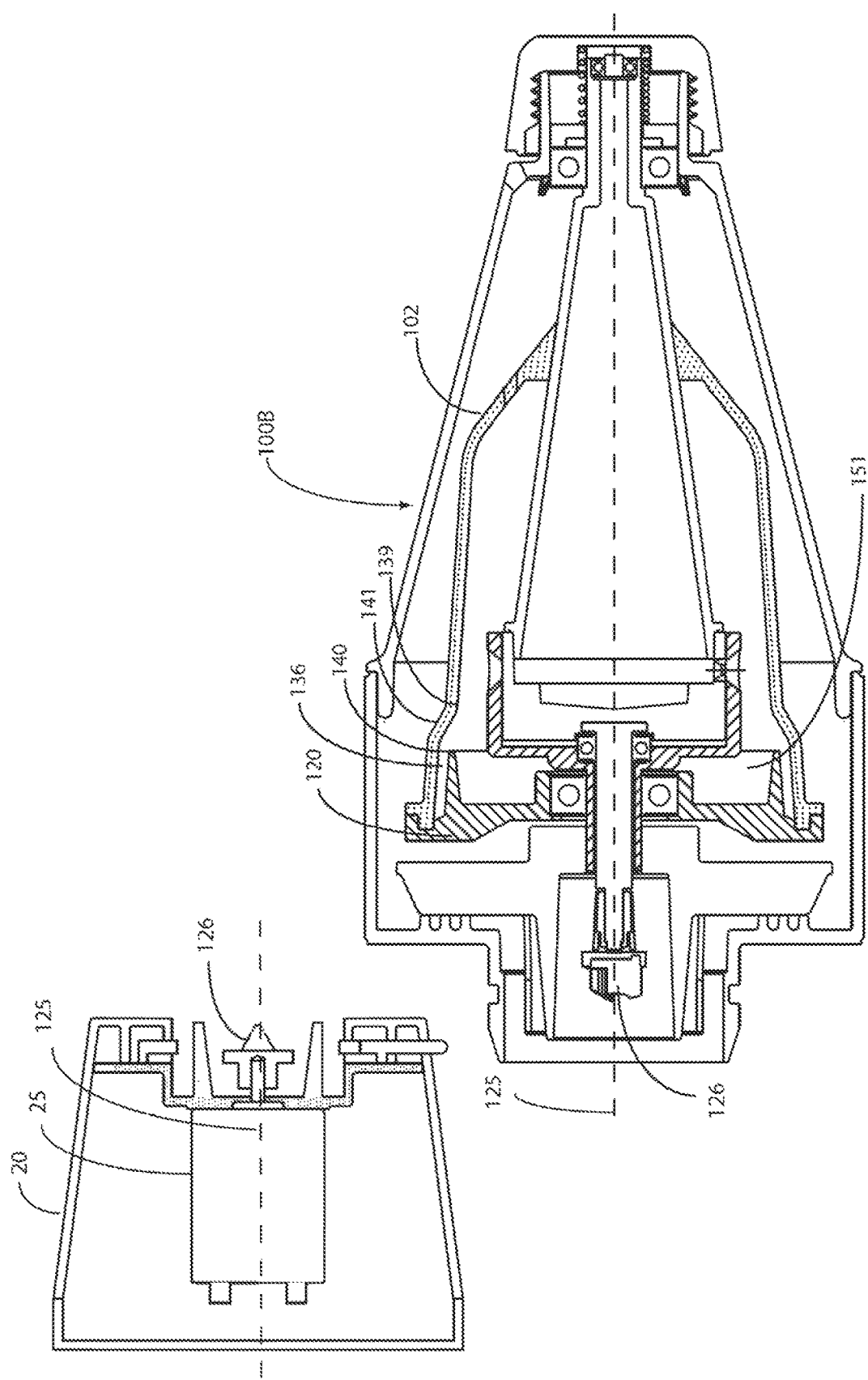
FIG. 2 is a cross section view of an alternate exemplary embodiment of the processing unit shown in FIG. 1, wherein the inner chamber includes an inflection, and also showing the base unit making up the centrifuge.

The exemplary processing assembly or unit 100A of FIG. 1, like the other processing units to be described later, is arranged to be releasably mounted on the base 20. Once mounted on the base, the centrifuge can be operated to rotate the processing unit at a high rate of speed (to be described later) about a central, longitudinal axis 125 of the processing unit. The means for effecting that rotation basically comprises a motor 25 housed in the base unit 20 (FIG. 2). The processing assembly is rotated upon activation of the motor 25 through a coupling 126. The coupling is preferably in the form of pair of keyed components that releasably mate together, such that the base unit and the processing assembly can be selectively engaged. While the various processing units and the base unit are shown horizontal in the figures of the drawing, it should be pointed out that in use the centrifuge is oriented so that the axis of rotation of the chambers is vertical, with the base unit disposed on some surface and supporting the processing unit above it.

It is preferred that the base unit 20 be reusable so that it can be used consecutively with multiple processing assemblies. It is, however, contemplated that the base unit can be disposable, if desired. The processing unit is, however, preferably disposable, but that is not mandatory providing that it can be sufficiently cleaned and sanitized for reuse. In the embodiment where the drive unit is reusable, the cost for the user can be kept lower than would be the case where the drive unit is disposed along with the rotatable separation unit. It is contemplated that the act of joining of the engageable components (i.e., the drive unit 20 and processing unit 100A) may trigger an automatic start-up reaction in the drive unit, in order to begin processing of the fibrous material. For example, by incorporating magnetic switches in the drive unit, the act of inserting the processing unit into the drive unit may wake up and optionally start the drive unit. Alternatively, the drive unit may include manually operated controls, to allow the operator to have complete control over some or all of the processing steps.

The processing unit 100A also includes an outer housing 101 in which the outer chamber 102, the inner chamber 103 and a stationary sleeve 117 are disposed. The inner chamber 103, stationary sleeve 117 and the outer chamber 103 will be described in detail later. The inner chamber is a hollow, tapered (e.g., conically shaped) member having a sidewall and a base. The outer chamber 103 is arranged to have the tissue to be processed introduced into its interior via an injection port 110. To that end, the inner chamber is arranged to be rotated about the central axis 125 whereupon the centrifugal force produced by the rotation causes the introduced tissue to be extruded through one or more extrusion holes 114 in the inner chamber. The stationary sleeve 117 is disposed between the inner chamber 103 and the outer chamber 102 and includes at least one outlet hole 115, which is arranged to receive the tissue extruded through the extrusion hole(s) 114 as each is brought into alignment with the outlet hole as the inner chamber rotates with respect to the sleeve 117. This action serves to cut or otherwise shear off the tissue extruded through the extrusion hole, thereby morselizing that tissue. The morselized tissue then enters into the interior of the outer chamber 102 as a slurry. The outer chamber is a hollow, tapered (e.g., conically shaped) member having a sidewall and a dish. As mentioned above, the outer chamber is also arranged to rotate about the central axis 125 by the operation of the motor of the base unit. That action causes the slurry material to stratify, with the higher specific gravity migrating away from the central longitudinal axis. The outer chamber includes an annular trap 136 located at the furthest radial distance from the central longitudinal axis. The trap is arranged to receive the portion of the slurry having the highest specific gravity, e.g., the concentration of multipotent cells when the centrifuge is used to process adipose tissue to enable those cells to be readily recovered from the trap, as will be described later.

The inner chamber 103 basically comprises a base 118 and a conical member 134, both being driven via a shaft 129, that is integrally fastened to the base 118. This inner revolving assembly is mounted in a sleeve bearing 119 and a large bearing 104. A stationery sleeve 117, and the sleeve extension 124 is placed around the inner rotating base 118, with the clearance between the sleeve 117 larger end and the base 118 set to a precise value, typically the tolerance is set in the range of 0.001 inch to 0.02 inch, and preferably 0.001 inch to 0.005 inch. The outer chamber 102 is mounted over the inner chamber 103 and is secured thereto at an upper joint 135. The outer chamber basically comprises a dish 120 secured to the sidewall of the outer chamber at lower joint 130. The dish 120 thus forms the larger end of the outer chamber, and is supported for rotation on a dish end bearing 121. The extension 124 of the sleeve 117 is pressed fit into a bottom plate 123, which is stationarily mounted with respect to the housing 101. Thus, in this embodiment, all three of components 123, 124 and 117 are stationary, in that they do not rotate when the centrifuge is activated. At least one extrusion hole 114 is provided in the base 118 of the inner chamber 103. The extrusion hole may be formed by inserting (e.g., pressing) a small plug 113 into a hole in the wall of the base 118, with the plug having an extrusion hole (or extrusion nozzle) 114 on its centerline and with a lead or chamfer 116 formed on the inner end of the hole. Although, only one plug is shown, it is contemplated that more than one plug may be provided, such as by being distributed at intervals around the circumference of the base 118. Alternatively, the opening of the extrusion hole 114 may be integrally formed in the sidewall of the inner chamber, e.g., the sidewall of base 118, rather than requiring a distinct plug or multiple plugs to be inserted into the opening(s). The entrance chamfer 116 can be of any angle or can be a radius, so as to prevent fiber agglomeration at the entrance chamfer. The extrusion hole 114 is shown adjacent to a conical outlet hole 115 in the sleeve 117. One or more outlet holes 115 may be provided in the sleeve 117, and as shown in cross-section in FIG. 1, two outlet holes 115 are depicted. Typically, more than one outlet hole 115 is usually used, often six, but any desired number can be used. By varying the spacing between the provided outlet holes, the size of the particle of fatty tissue that is ejected (extruded) through the outlet holes 115 can be controlled, for a given rotational speed of the centrifuge. As the chamber 103 is rotated adjacent to the static sleeve 117, the conical outlet hole 115 in sleeve 117, as shown in FIG. 1, acts as a blade to sever portions of material exiting through the extrusion hole 114, and in this manner, serves to break down the collagen fiber network in the starting material, to form a morselized material. It is contemplated that any kind of opening having a sharp edge could be used, such as a square hole, or alternatively, a knife blade mounted along one side of a round hole. The conical outlet angle of the outlet hole 115, as shown, is depicted as around a 60 degree included angle, but other angles can also be used.

At the small diameter end of inner chamber 103 a spring 108, a stepped washer 107 and an end-cap 106 are located. The end cap includes threads 111 and is arranged to be threadedly secured on opposing counter-threads provided on the upper neck 105 of the outer housing 101. These engaging threads allow the end cap 106 to be rotated, thus providing for compression of the spring 108, which when compressed, serves to preload the large bearing 104 via the stepped washer 107. The preload is transmitted via the inner chamber 103 to a sleeve bearing 119. The sleeve bearing 119 is located between the base 118 of the inner chamber 103 and the stationary sleeve 117. Thus, the preload is provided to the sleeve extension 124, from thence to the plate 123 and from thence to the outer housing 101. A small bearing 109 is mounted in the small diameter end of revolving inner chamber 103 in order to allow the passage of a non-rotating needle or cannula (or other tubular member) into the revolving chamber through the injection port 110, as the inner chamber 103 is rotating.

Although the sleeve 117 has been described as stationary or non-rotating, it is contemplated that in an alternative embodiment the sleeve may also rotate. However, in such a case there must be difference in the rotation rates of the inner chamber and the sleeve. In particular, in order to achieve the goal of severing portions of material exiting through the extrusion hole 114 to form the morselized material, there need be some difference between the rate of rotation of the inner chamber and that of a rotating sleeve. The rotation of the sleeve may be either in the same, or opposite, direction of rotation as that of the inner chamber. For this embodiment, so long as there is momentary alignment of the extrusion hole 114 and the conical outlet hole 115 of the sleeve, then the exiting (extruded) material may be severed into smaller particles (morselized).

In operation of the various exemplary embodiments described herein, adipose tissue can be obtained from a patient by known techniques, including liposuction or surgical excision. In the case of tissue obtained by liposuction, the fatty tissue and tumescent solution mixture are likely to be in about a 1:1 ratio and will have passed through suction cannula orifices that will have reduced the fat fragments to a size of about 2 mm. This biologic mixture can be fed straight into the various embodiments of a centrifuge device described herein, via the injection port 110 or stationary tube 235, as appropriate. Alternatively, In the case of fatty tissue obtained via surgically excision, the fat will typically be removed from the patient as a semi-coherent mass, in contrast to the tissue collected as particles through liposuction. In the case of surgically excised fat, the fat should be broken up into smaller pieces, and then is to be mixed with portions of liquid, typically with saline or tumescent solution, up to two times the volume of fat, though it is contemplated that other proportions may be suitable as well. The mixing of the harvested fat and mixing liquid may be performed by passing the mixture to and fro between syringes having nozzles of about 2 mm before placing in the centrifuge device.

In operation of any of the various exemplary embodiments described herein, the adipose tissue harvested may optionally be treated with an additive, such as a biologically active agent. It is contemplated that one may wish treat the adipose tissue with, for example, drugs, antibiotics, cellular modifiers, pH modifiers, enzymes, blood products (e.g., whole blood, platelet rich plasma (PRP), red blood cells, platelet poor plasma (PPP), bone marrow aspirate (BMA) or bone marrow aspirate concentrate (BMAC)), prior to, or during the processing of the adipose tissue in the various exemplary embodiments described herein. Alternatively, one or more preservatives or anti-coagulants (e.g. heparin, coumarin, ethylene diamine tetra acetic acid (EDTA), citrates (e.g., Anticoagulant Citrate Dextrose A (ACDA), oxalate) may be added alone, or other additives, to the adipose tissue prior to, or as it is being processed in the various exemplary embodiments of the devices described herein. It is contemplated that additives may beneficially aid in separation of cells during centrifugation, may alter the behavior of the cells in the harvested sample for processing as described herein, or enable the storage of the harvested tissue sample for subsequent processing as described herein. For example, the addition of ACDA may prevent coagulation, allowing storage of the solution containing red blood cells or platelets, or additionally, the ACDA may serve to alter the morphology of stem cells and platelet cells. For example, Applicants believe that adding ACDA to the charge of biologic mixture may be beneficial, in the case of platelet cells typically having a plate-like morphology, may convert to a more spherical morphology, thereby beneficially affecting the ability of the platelet cells to separate by specific gravity, as the more spherical shape of the cell may maneuver more easily through the other constituents of the biologic mixture, e.g., adipose tissue particles.

As mentioned earlier, the centrifuge device of FIG. 1 is mounted with its spinning axis, i.e., central longitudinal axis 125, oriented vertically. The rotating chambers are driven by the drive unit via a coupling 126 to about 15,000 rpm, or the equivalent of 4000×G at the inner chamber 103 periphery. The charge of fatty tissue and solution mix is injected into the top of the rotating device (through small bearing 109) into the inner chamber, using a syringe with a narrow cannula. As the charge is rotating within the inner chamber 103, the charge will then generate pressure from the centrifugal effects and attempt to extrude from the extrusion hole 114. When the extrusion holes 114 of the base are in radial alignment with outlet holes 115 of the sleeve, as shown in FIG. 1, the fatty tissue charge can extrude from the extrusion holes 114. However, as the inner chamber 103 revolves, the hole 114 moves into a closed area where the sleeve 117 has no hole. The period of time that the extrusion hole 114 is open is controlled by the speed of rotation and the size of the extrusion holes 114 and sleeve outlet holes 115. The extrusion flow rate of the charge is controlled by the pressure, which is in turn derived from the speed of rotation which creates the centrifugal field. By selection of hole sizes and rotation speed, the length of extruded charge cut off can be determined. With extrusion holes 114 of about 1.7 mm in diameter, sleeve outlet holes 115 of about 3 mm diameter, and a chamber 103 rotation speed of approximately 15,000 rpm, the extruded fragments can be cut into less than 1 mm lengths and appear as a slurry of morselized fatty material. In an embodiment having 6 outlet holes 115 in the sleeve, a charge of 30 mL passes through the extrusion holes 114 in about 20 seconds. Once the charge has been morselized, and has passed into the outer chamber 102 as a slurry, the rotational speed may then be reduced to approximately 10,000 rpm (equivalent to 3500×G for a 60 mm outer chamber diameter), and the centrifugation continued for an adequate period of time, e.g., approximately 2 minutes, to ensure separation of the desired constituents.

During this centrifugation process, the fatty constituent of the material tends to migrate toward the central longitudinal axis 125, and the heavier cells and aqueous solution tend to move toward the outer walls of the outer chamber 102. The heaviest density fluid (having the highest specific gravity), containing the highest concentrations of multipotent cells, moves to the outermost diameter, to the annular trap 136. That trap basically comprises an angularly extending channel, though the size and shape of the trap may be modified to capture different fractions of the biologic mixture. For example, the trap may not be angled as shown, but rather may be a channel that is arranged parallel to the axis of rotation 125. In any event, when the rotation of the centrifuge chambers is stopped, the fraction of the biologic mixture not within the trap 136, and within the chamber 102, then drops into a cavity 151 in dish 120 by gravity, and the more viscous fat material collapses onto this liquid. Thus the multipotent cell containing liquid can be isolated in the trap 136 for harvesting. The liquid containing the majority of multipotent cells residing in trap 136 may then be removed by syringe and a shaped cannula, via ports 138 and 137 in the housing 101 and the outer chamber 102, respectively.

For greater ease of manufacture, the inner chamber 103 and outer chamber 102 are arranged to rotate together, in a synchronous fashion, however, in this and in the other embodiments described herein, it is contemplated that the centrifuge could be arranged so that the inner chamber 103 and outer chamber 102 rotate in an asynchronous manner. Thus, the inner chamber 103 may rotate at a first speed, so long as that rotation creates a centrifugal field which will generate sufficient pressure upon the charge of tissue, so as to cause the ejection of the tissue material through the extrusion hole 114; while the outer chamber 102 rotates at a second speed, whether in the same or different direction of rotation, so long as the rotation creates a centrifugal field, so as to effect the stratification of the morselized slurry material.

It has been observed that fat of different composition behaves differently in the centrifuge device. Whereas a portion of the liquid having the highest specific gravity does indeed move to the outer diameter during centrifugation and a portion of that highest specific gravity fluid fills the trap 136, the residual fat may, or may not, emulsify into a stable creamy paste. In those instances where the residual fat is in the form of a stable paste, the paste material will be self-supporting, at least for a few minutes, rather than flowing, as would a paste that is not self-supporting. If the paste is relatively stable, upon ejection through the extrusion hole 114, the paste may coat the inner wall of the outer chamber 102 at smaller diameters, nearer the cone apex, with the paste remaining in place against the wall, even after the rotation of the centrifuge has been stopped. Alternatively the fat can remain as small granules, that do not adhere to either the outer chamber 102 wall or to each other, rather these granules remain free to move relative to each other, in contrast to a material having a self-supporting paste consistency. In these instances, when the chamber stops spinning, the fat granules tend to fall toward the chamber's large diameter end and may disturb the higher specific gravity fluid that has been collected in the trap 136, potentially reducing the concentration of that fraction. To minimize the possibility of the granules of fat interfering with the liquid collected in the trap, the centrifuge may include an alternative processing unit 100B as shown in FIG. 2. In that embodiment the wall of the outer chamber 102 includes an off-set or inflection 141 which serves to ensure that the inner diameter 139 of that portion of the outer wall 102 is reduced to about that of the trap lip 140. This arrangement allows the fat granules to drop into the basin 151 of dish 120 and miss the trap 136.

Figure 3:
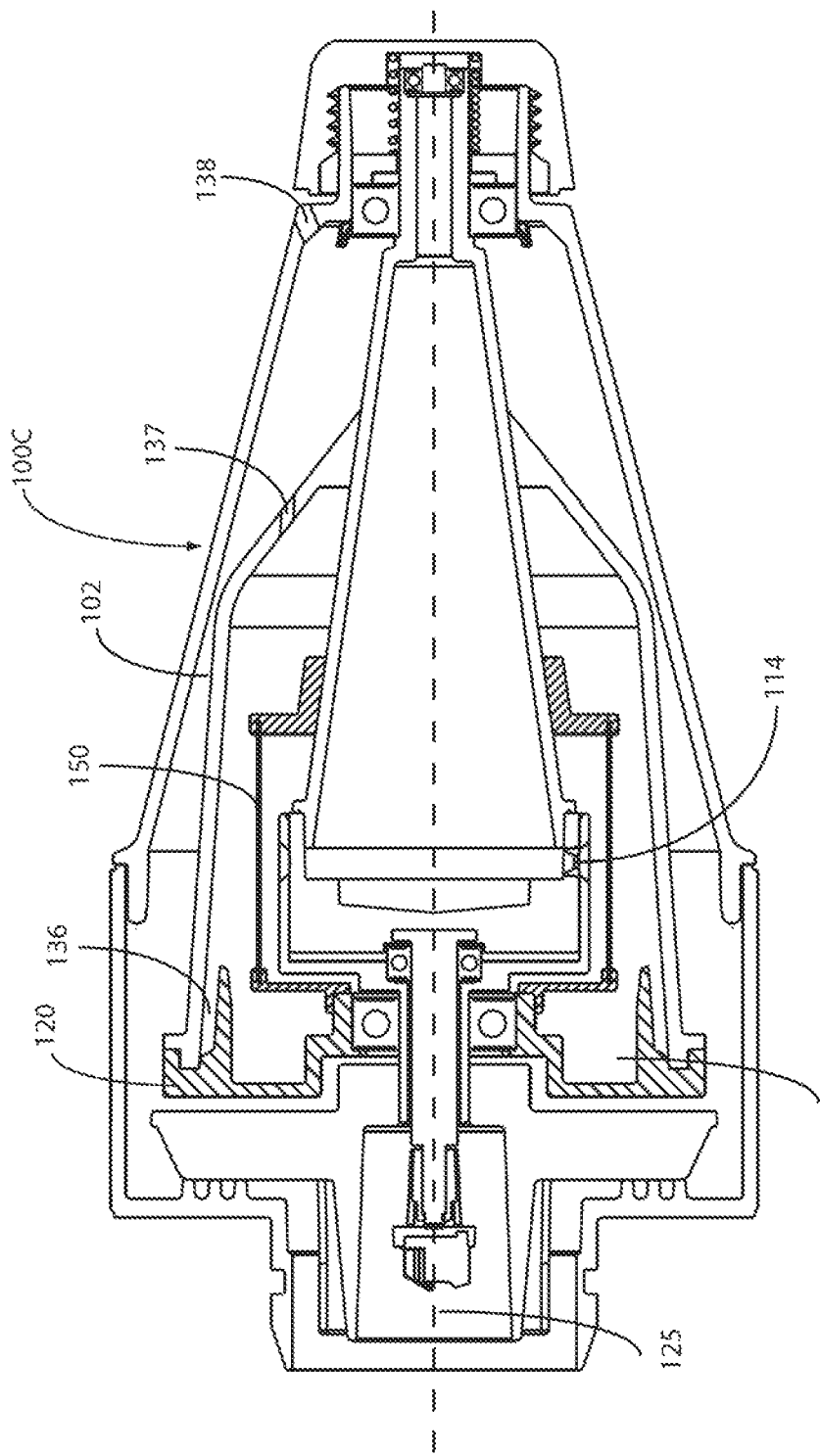
FIG. 3 is a cross section view of an alternate embodiment of the processing unit of FIG. 1 additionally comprising a screen element between the inner chamber and outer chamber.

Referring to FIG. 3, there is shown another alternative embodiment of a processing unit 100C. This embodiment includes screen element 150 located between the stationery sleeve 117 and the outer chamber 102. The screen 150 is a mesh-like element 150 and is arranged so that the slurry which exits from the extrusion holes 114 encounters the screen, thereby morselizing the slurry into smaller particles that pass through the screen. The screen 150 is arranged to rotate along with the extrusion holes 114, thus the screen need not necessarily extend entirely circumferentially around the sleeve 117. Instead it may be radially aligned with the exit holes 114. However, for ease of manufacture, one may incorporate the screen 150 as a concentric ring surrounding the sleeve 117. In operation of the device, as the fatty tissue slurry exits the extrusion hole 114 under pressure generated by the rotation of the device, it impacts on the screen 150. The screen can be a wire mesh or a perforated tube, with holes of a diameter most likely in the range 1 mm to 0.25 mm, but in general of whatever size best breaks down the adipocyte binding structure. Ideally, the screen is of metal wire mesh construction, though plastic mesh may work as well. As the screen is revolving, any slurry of fat, fibers, and liquid will experience significant centrifugal forces to propel portions of the slurry through the screen. Experiments have shown that the slurry is broken down completely, leaving only fibers on the screen, and a high count of mononuclear, including multipotent cells in the liquid. Like the operation discuss above, the continued rotation of the chambers of this embodiment of the centrifuge causes the liquid components that have flowed through the screen to separate by specific gravity in the outer chamber 102, with the highest specific gravity components accumulating in the trap 136. As rotation is halted, the remaining fluid collects in the basin 151. The multipotent cell rich liquid in the trap 136, may then be harvested by directing a needle or cannula through ports 137 and 138 and into the trap 136.

With this embodiment of the device, and when processing porcine deep adipose tissue, it is possible to retrieve up to 90% of the viable mononuclear cells from the fat samples.

Figure 4:
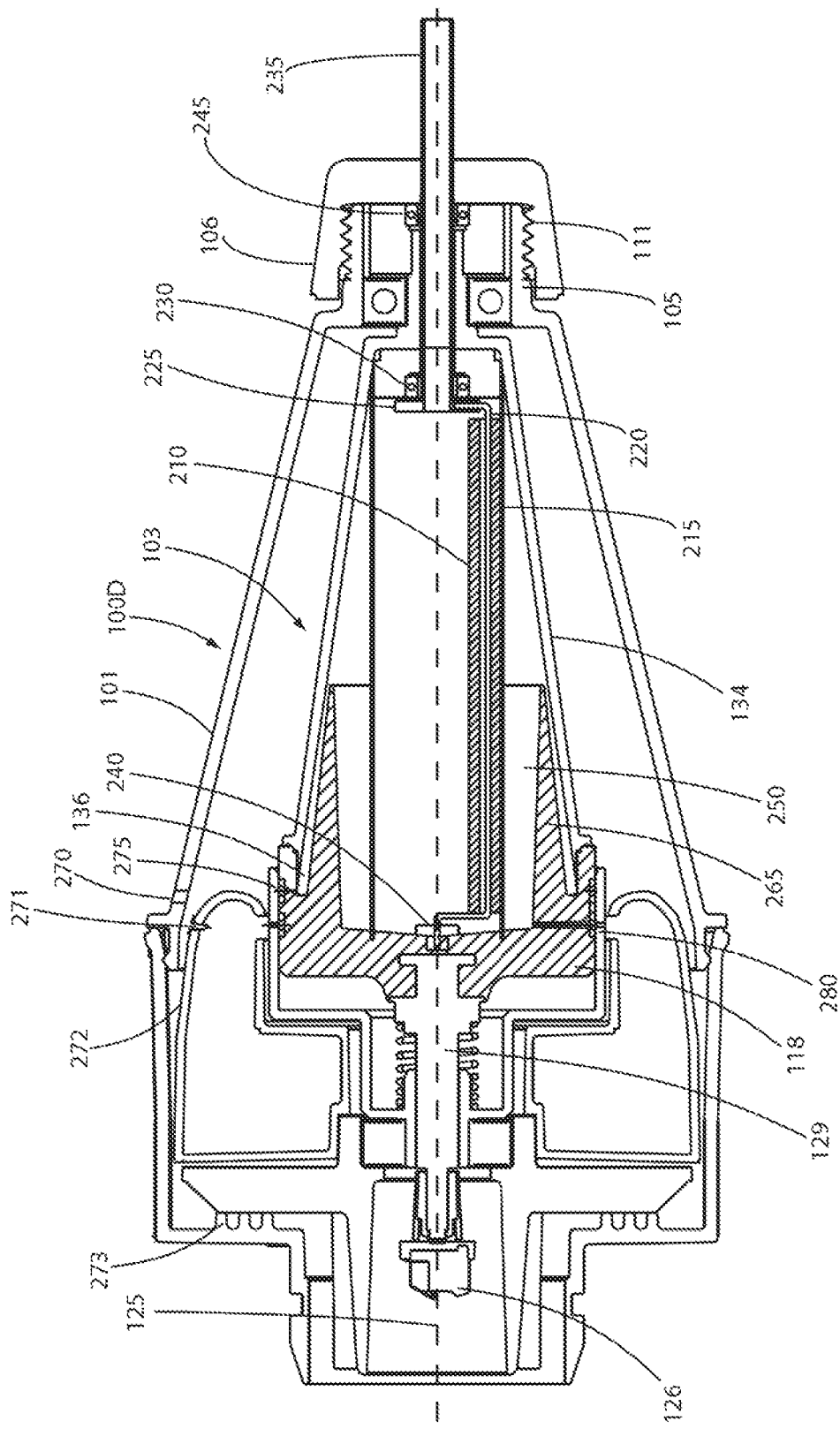
FIG. 4 is a cross section view of another alternative embodiment of a processing unit of a centrifuge constructed in accordance with this invention, wherein the processing unit includes a screen element and a roller element.

FIG. 4 shows another alternate embodiment of the processing unit 100D. This processing unit is also arranged to be driven from a motor having a drive axis, and housed in a base unit, as has been described previously. Unlike the previously disclosed processing unit embodiments, the processing unit 100D of FIG. 4 includes a roller element 210, acting in concert with a rotating screen 215 to morselize the tissue provided within the inner chamber, prior to causing the tissue to be separated by centrifugation. This embodiment includes a revolving inner chamber 103 having a conical sidewall 134. An annular screen element 215 is located within the inner chamber 103 and extends concentrically around the central longitudinal axis (i.e., the axis of rotation). The screen element extends from where it is joined to the base 118 of the inner chamber, up to the point where it meets the chamber's sidewall. The screen thus divides the inner chamber 103, so that material passing from a region within the annulus of screen element 215 to the outside of the screen element must necessarily pass through the openings provided in the screen element. The screen element is a mesh-like member that may be a metal or polymer wire material, or alternatively a perforated sheet providing openings sized to pass fluid material, but retain much of the fibrous material. It is envisioned that the openings will be uniformly or non-uniformly sized between 0.002 and 0.040 inches. To aid in passing the tissue material through the screen element, a roller element 210 is provided adjacent to, and arranged to roll against, the inner surface of the screen element. The roller element is mounted on an axle 220. The axle may be of any sort known in the art. As shown in FIG. 4, the axle may be a formed stiff wire that extends through the center bore of the roller, and the wire is mounted so that it may be secured in a static (stationary) position within the inner chamber. In this embodiment, the upper end of the wire that forms an axle 220 that is fixed to a flange 225 at the end of a stationary tube 235 and which extends through an opening in the end cap 106. The flange 225 and the stationary tube 235 feature a hollow bore extending through their interior, which serves as the entry port for directing tissue material into the device for processing. The flange 225 and stationary tube 235 are isolated from the rotation of the inner chamber 103 by flange bearings 230 and a port bearing 245. The lower end of the formed wire that makes up the axle 220 is directed into a bushing 240, placed in the concentric center of the base 118 of the inner chamber 103, in line with the axis of rotation of the inner chamber. The bushing 240 serves to isolate the static axle 220 from the rotation of the inner chamber 103. Thus, the roller element 210 can effectively be made to roll around the interior surface of the screen element 215 by keeping the roller axle 220 stationery as the screen 215 and inner chamber 103 revolve.

It is contemplated that there may be a benefit to utilize a roller element 210 which is provided with a freedom of movement, such that it can articulate, as it rotates about the static axle 220. Examples of possible articulation mechanisms are shown in FIGS. 6A and 6B. By providing a force at the mid-length of the roller, and clearance over the axle 220, the roller can move relative to the chamber's axis of rotation as it engages lumpy portions of the tissue material. FIGS. 6A and 6B show a detailed expanded view of the roller element 210, on the axle 220, against the screen element 215. In these embodiments, the roller is able to float against the screen element 215, by the nature of the deflection in a direction perpendicular to the axis of rotation, which is allowed by the spring wire formed as axle 220. Further, the roller element 210 is able to yaw, demonstrated as the rotation axis of the roller element 210 leaning, as the roller element 210 encounters the tissue against the screen element 215. The ability to yaw is provided as the roller may pivot on the axle 220.

Referring again to FIG. 4, it can be see that the inner chamber 103 features a tapered sidewall 134. The base 118 of the inner chamber 103 is shaped so as to provide a tapered surface as well, relative to the axis of rotation 125, provided by the wedge 265. As is depicted in FIG. 4 the trap 136 is in this case defined by the outer surface of the wedge 265 and the inner surface of the conical sidewall 134. The trap 136 is preferably annular, though it is contemplated that alternate shapes may suffice, for example by being lobed. The trap, as depicted in FIG. 4 in cross section, appears as an angled passageway, with an innermost portion at the entrance into the trap, where the mixture component enters from the central area of the rotating chamber, and adjacent to the tapered end of the wedge 265. The entrance to the trap forms the end of the trap closest to the axis of rotation 125. The trap 136 also features an outermost portion, at the end having the greatest radial distance from the axis of rotation 125. Alternatively, the trap 136 may not be angled relative to the axis of rotation, but rather may be arranged parallel to the axis of rotation. At the largest outside diameter of the trap, there is provided a first port 275, which is selectively openable, such as through valving, so as to allow access to the trap to harvest the processed material fraction contained therein. An access opening 270 may be provided in the outer housing 101 to facilitate access to the first port 275. In particular, when the first port 275 is to be accessed, an access needle or cannula (not shown) may be directed through aligned openings, so as to allow the harvest of the processed material fraction in the trap 136. This may be accomplished by placing into alignment the access opening 270, the first port 275, and the sealed port 271. That port may be in the form of a duckbill valve or a self-sealing septum in the wall of a container or vessel 272. The container 272 is an annular member located within the lower portion of the processing chamber 100D and its function will be described later. The alignment of the access opening 270, the first port 275, and the sealed port 271 may be controlled by various means known in the art, for example, by manually rotating a portion of the exterior housing. Cams 273 are provided projecting inward from the bottom portion of the housing to selectively adjust the vertical positioning of selected elements in the device. Alternatively, the first port may be selectively openable, and closeable, during the rotation of the inner chamber 103, such that at least a portion of the material contained within the trap 136 may be automatically ejected into a collection area that may be accessed later.

In operation of the embodiment depicted in FIG. 4, a charge of fat and solution, such as blood, saline, water, tumescent solution, is inserted through the stationery tube 235. Once the charge has been inserted, the inner chamber 103 and screen element 215 are rotated via the coupling 126, by the motor at a first speed, while keeping the roller axle 220 stationery, for a defined first period. During this first period of rotation, the fat will tend to spread along the inside of the screen element due to the effect of the centrifugal field created by rotation of the chamber, and the roller element 210 will force the fat through the mesh of the screen element 215, as the fat passes between the roller 210 and the screen element 215. The tissue material becomes morselized into smaller particles by being forced through the openings in the mesh, and further, a portion of the collagen fibers become separated from the other materials in the charge and are retained on the mesh by becoming draped around the screen wires. It is also possible that upon encountering the roller and being forced through the screen, the collagen fibers in the fat material are cut by the mesh, and thus the tissue charge is morselized into smaller particles sizes. Subsequent to the charge being forced through the mesh, the inner chamber 103 is then rotated at a second speed to centrifuge the morselized material, and based on the specific gravities of the components making up the morselized material, separate the mixture of liquid and fat for a second defined period of rotation. During this second period, it is believed the heavier multipotent cells tend to migrate through the liquid to the outermost surfaces in the inner chamber. In particular, while the inner chamber 103 is rotating about the axis 125, the centrifugal field created will create stratification of the constituent components by their specific gravity, as the centrifugal field will urge the highest specific gravity components away from the axis of rotation (i.e., outwards), whereupon they will encounter the tapered walls of the inner chamber 103 and the inner surface of the wedge 265. Continued rotation will cause these more dense components to displace less dense components, as the higher specific gravity components gather along the tapered sides out from axis of rotation, whereupon the highest specific gravity components will then enter into, and accumulate, in the trap 136. When the rotation of the inner chamber 103 is stopped at the end of the second defined period, the residual liquid settles in the base 118 and is collected within the dished area 250, defined by the area being surrounded by wedge 265 on its perimeter, and having the base 118 as a bottom surface. The fat material that had been held towards the center of the centrifugal field, due to the lower specific gravity, will frequently have the consistency of a paste, and either tends to remain stuck to the upper portion of inner surface of the sidewall 134, or alternatively the fat material may settle within the dished area 250. The liquid containing multipotent cells remain in the trap 136, on the outside of the wedge 265, and may be retrieved by using a needle or cannula (not shown) to suck out the fluid and cells from the trap 136. As mentioned earlier, the embodiment shown in FIG. 4 also provides a first port 275, which may be selectively opened and closed by valving, to allow removal of higher specific gravity components from the trap 136. Furthermore, there may also be provided a second port 280, which may be selectively opened and closed by valving, to allow removal of lower specific gravity components from the dished area 250. The second port 280 may be located at the base of the wedge 265 within the dished area 250. By selectively opening the first or second port for a period of time while the chamber is being rotated, one may fine tune the specific gravity of the cellular concentrate fraction that is collected within the inner chamber 103 in a manner similar to that described in co-pending U.S. patent application Ser. No. 13/396,600, which is assigned to the same assignee as this invention, and whose disclosure is incorporated by reference herein. The centrifuge of that application is particularly suitable for obtaining a desired fraction from a biologic liquid mixture, such as platelet rich plasma from whole blood, or stem cells from bone marrow aspirate, however that application provides no capacity for morselizing tissue structure in the biologic mixture, such as adipose material.

In any of the various embodiments described herein, wherein there is a chamber comprising one or more of: a wedge element 265, a first port 275, or a second port 280, the ejection of one or more portions of the biologic mixture within the chamber may be accomplished as follows. The biologic mixture, having been sized by any of the methods described herein, is then rotated within the rotatable chamber to cause the contents to separate by specific gravity. Thus, an outer band of high density fluid (having a higher specific gravity) will form, upon rotation of the chamber, at the outermost surface of the chamber (farthest away from the longitudinal axis 125. An inner band of low density fluid (having a lower specific gravity) will form in the liquid closest to the center of the chamber (closest to the longitudinal axis 125). In between, the outermost and innermost layers, will be at least intermediate layer comprising at least one fraction having a specific gravity between that of the innermost and outermost layers. It is contemplated that the rotation of the chamber and its contents will form an air core, where there is no fluid at the longitudinal axis, so long as the volume of fluid in the chamber is less than the volume of the chamber itself. In those embodiments, where there is a need to eject out of the chamber the heaviest fraction of the biologic mixture, for example, where the fraction having the highest specific gravity contains almost no multipotent cells, this outermost fraction may be discharged through selectively openable first port 275 having an inlet within the chamber at the greatest distance from the longitudinal axis, such that when the valving for the first port is opened, the rotation of the chamber will create a centrifugal force urging the liquid with the highest specific gravity to exit the chamber through the first port 275. The first port is to remain open to allow at least a portion of the highest specific gravity fraction to exit the chamber, whereupon the first port may be closed, whether by action of the operator monitoring the location of an interface, on the tapered surface of the chamber, or operation of an automatic valve. For example, the operator may monitor a color interface that occurs between red blood cells and the multi-potent stem cell fraction, which can be detected through a transparent sidewall of the centrifuge devices described herein. Furthermore, in those embodiments where there is a need to eject the lightest fraction of the biologic mixture, for example, where the fraction having the lowest specific gravity contains almost no multipotent cells, this innermost fraction may be discharged through selectively openable second port 280, having an inlet located within the chamber at a radial distance that is less than that of the radial distance for the inlet of the first port 275, such that when the valving for the second port is opened, the rotation of the chamber will create a centrifugal force urging the fraction of the liquid with the lowest specific gravity to exit the chamber through the second port 280. The second port may remain open to allow at least a portion of the lowest specific gravity fraction to exit the chamber, whereupon the second port may be closed, whether by action of the operator or operation of an automatic valve. In many instances, the second port may be allowed to remain open until the air core, expanding as fluid exits chamber, reaches the entrance to the second port 280, thereby cutting off the flow of fluid out of the second port. In this manner, the inner band of lower density fluid (having a lower specific gravity) and optionally, fat, can be discharged through the second port 280 and into the container 272, leaving the desired concentrate fraction within the dished area 250, at the center of the inner chamber 103, once the rotation ceases. The at least one fraction, having a specific gravity intermediate that of the 2 ejected fractions, will remain within the chamber, and may then be collected by insertion of a cannula into the chamber.

Figure 5:
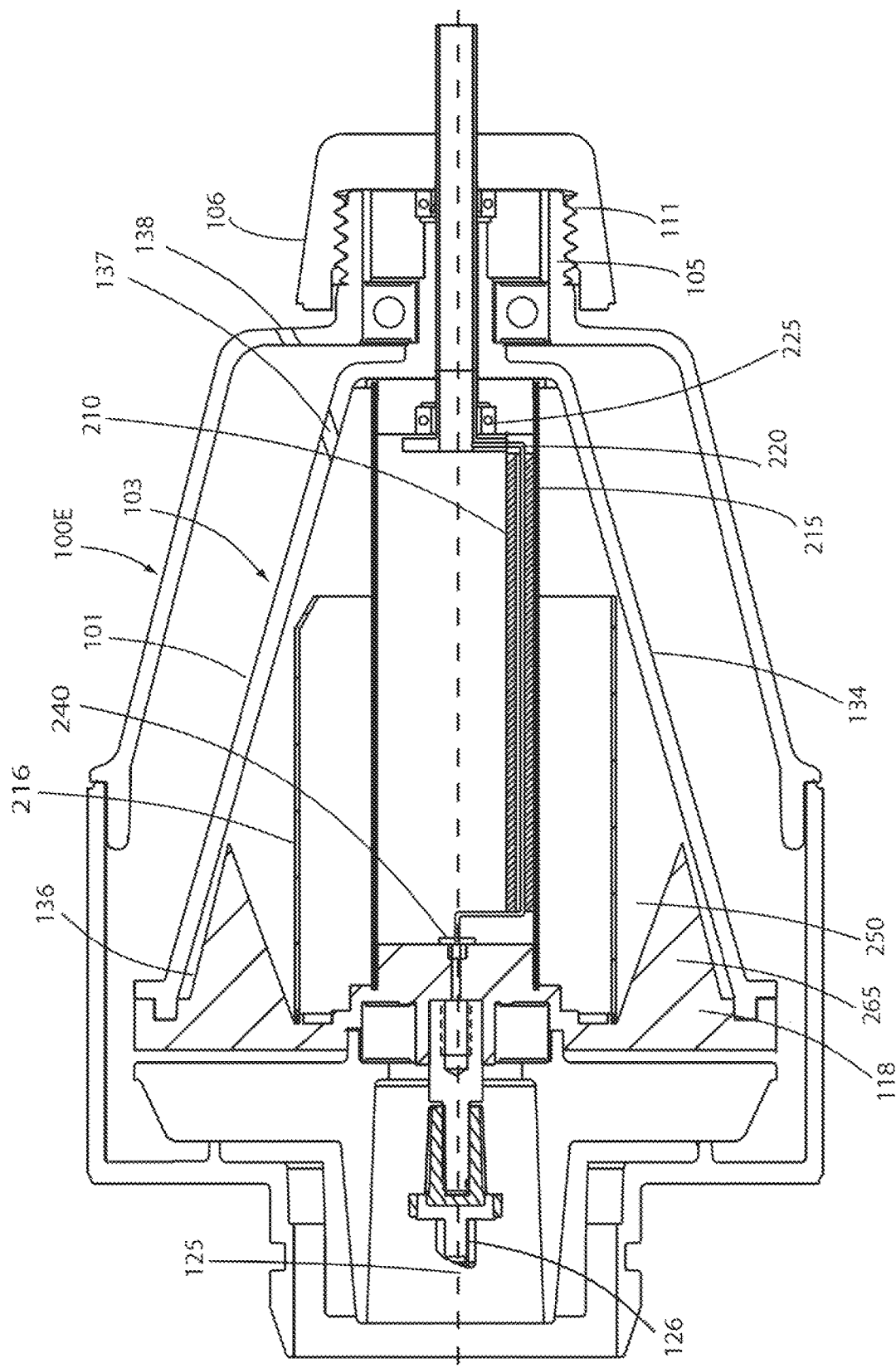
FIG. 5 is an enlarged cross section view of still another alternate embodiment of a processing unit of a centrifuge with a screen element and roller element constructed in accordance with this invention.

FIG. 5 shows yet another alternative embodiment of a processing unit 100E. That unit, while somewhat different structurally, operates similarly to the processing unit 100D shown in FIG. 4, in that the unit 100E includes a screen and roller arrangement that serves to morselize the tissue material, as has been described above. In the embodiment of FIG. 5, a charge of tissue is delivered to the inner chamber 103, and the inner chamber is rotated. The centrifugal field generated by the rotation will cause the charge of tissue to spread along the screen element 215, whereupon the tissue will be forced through the screen element under the pressure of the roller 210, rotating around a roller axis 220. As before, the passage through the screen element morselizes the tissue, and may retain or cut, the collagen fibers in the charge. The morselized tissue will continue to rotate with the rotation of the inner chamber, causing the stratification of the components of the morselized tissue to separate by specific gravity, with the lowest specific gravity components being displaced at the perimeter by the higher specific gravity components, as the higher specific gravity components are driven away from the axis of rotation 125.

In this or the other processing unit embodiments having a screen element 215, there may be included an optional secondary screen element 216. In such a case, the morselized tissue that has been directed through the screen element 215, will encounter the secondary screen element 216, as the material is directed outwards by the force of the rotation. The secondary screen element 216 is similar to the screen element 215, except that it has a smaller average opening size. While the secondary screen 216 may serve to further morselize the tissue, it is primarily intended to capture the fibrous material that does not readily pass through the openings, while passing the liquid and non-fibrous material therethrough. Use of this arrangement may benefit from reducing the rotational velocity while the processed material is encountering the secondary screen, so as to avoid having excessive centrifugal forces propel the material through the screen, where a slower rotation would aid in capturing the fibrous material against the screen while the liquid is urged through the openings.

As should be appreciated by those skilled in the art by reference to FIG. 5, while the rotation is ongoing, the highest specific gravity components will, under the force generated by the inner chamber's rotation, accumulate in the trap 136.

Upon cessation of rotation of the inner chamber 103, all of the material that is not retained within the trap, will fall, under the influence of gravity, into a dished area 250 in the center of the inner chamber. A cannula, needle or tubing may then be inserted through an access route created by ports 138 and 137 near the top of the device, optionally directed through an opening provided near the top of the optional secondary screen element 216, and directed into the trap 136, so as to harvest the heaviest specific gravity component, including the multipotent cells, while leaving the non-desired constituents within the dished area 250.

In the various embodiments described herein, the angle of the inner chamber and wedge, relative to the axis of rotation, will affect how forcefully, and thus how quickly, the stratification of the various components will occur. For example, in an embodiment where the angle of the inner chamber and wedge is shallow, the separation of the constituents will require an increased period of time of rotation, or alternatively higher rotation speeds may be required to drive the separation. By contrast, in an embodiment where the inner chamber and wedge are at a steep angle, off the axis of rotation 125, this steep angle will tend to produce a more forceful and rapid separation of the components. The angle required may be tailored to the viscosity of the fluid being processed. For example, where the charge of tissue is of a high viscosity, it is believed that a steep angle will allow more effective movement of the heaviest components through the fluid. Alternatively, where the charge of fluid is less viscous, it may be possible to employ a shallow angle, and still achieve adequate separation of the constituents. The goal of achieving rapid separation of the constituents is vital, as it is believed that extended duration of the exposure of living cells to elevated G forces during separation may negatively affect the viability of the cells. Thus, it is believed that minimizing the period of time in which the cells are rotated at high speed will lead to better viability of the processed cellular material. In practice of the various embodiments described herein, it is anticipated that the angle of the inner chamber and wedge will likely be between 5 degrees and 30 degrees, but angles of up to 45 or 60 may also work adequately.

In the various embodiments described herein, there may also be a benefit in aiding in the separation of the multipotent cells from the fibrous collagen network in the biologic mixture, such as by adding a volume of saline or other fluids (e.g., blood, bone marrow aspirate, or other body fluids, buffered solutions, cell culture media, detergent solutions, therapeutic solutions such as antibiotic, or anti-coagulants, etc.), as has been discussed previously. This additional fluid added to the harvested fatty tissue may serve to decrease the overall viscosity of the biologic mixture, which will in turn provide for more effective movement of the constituents of the mixture into stratified layers upon exposure to rotational forces. Additionally, the added fluid may enhance the separation of the desired cellular concentration from the other portions of the tissue sample. For example, the addition of whole blood or bone marrow aspirate, when separated by density, will result in the platelet-rich buffy coat comingling with the multipotent stem cells of the adipose tissue sample, as they would have similar specific gravities. The red blood cells, due to their highest specific gravity in the combined sample, would tend to accumulate at the outside layer within the rotating chamber. The plasma of the whole blood will form a separation layer between the multipotent cells and the fatty tissue. The platelets will likely form a layer adjacent to and/or intermingle with the multipotent cells. Furthermore, the addition of whole blood or bone marrow aspirate would also provide a visual indicator by color. Radial stratification would occur with layers forming, in order from the outermost to the innermost, with the red blood cells outermost, the multipotent cells and platelets next, clear plasma next, and the fatty tissue radially innermost, with the red blood cell boundary marking the edge of the fraction with the desired cellular constituents. Additionally, the addition of a liquid to the adipose tissue would likely serve to dilute out the epinephrine and lidocaine that may have been added for the collection of the fat sample.

Furthermore, it is contemplated that there may be a benefit to the various embodiments described herein by providing an agitation step after the morselization step, wherein the centrifuge device is operated in a manner that would impart a gentle, mixing movement to the biologic mixture, so as to ensure the cells are further separated from the fibrous network. The gentle mixing would thereby serve to avoid subjecting the cells to the potentially harmful effects of extended high G forces to achieve separation of the cells from the fibrous network, as it is believed that extensive periods of rotation at high speed may be detrimental to cell viability. This gentle mixing action may be achieved by random orbital movement, such as rocking off-axis, or alternately starting and stopping the rotation of the device, or varying the rate of rotation of the device. For example, the device may be rotated in an oscillating manner, at low frequency (e.g., less than 10 Hz, preferably around 1 Hz) and subjecting the cells to low G forces, in order to free the multipotent cells from the fatty and residual fiber network, or mix in additional fluid into the charge of tissue. The effect of the mixing may be enhanced by including projections, such as fingers, ribs or radial fins, extending into the rotating chamber. Such projections can be arranged as vertical elements, spiral elements, or combinations thereof, on the surface of at least one of the wedge 265, the outer surface of the mesh of the screen element 215, the inner surface of the conical sidewall 134, and the base 118, so long as a mixing feature is extended into the dished area 250. The oscillating motion would be quite similar in operation to that of a conventional clothes washing machine, where the alternating start-stop, and optionally, oscillating movement, all at much lower speeds than would be required to achieve centrifugal separation, should not result in significant reduction of cell viability, all the while providing the benefit of aiding in mechanically disassociating the cells from the fatty and residual fibrous material and other constituents of the biologic mixture.

Figure 7:
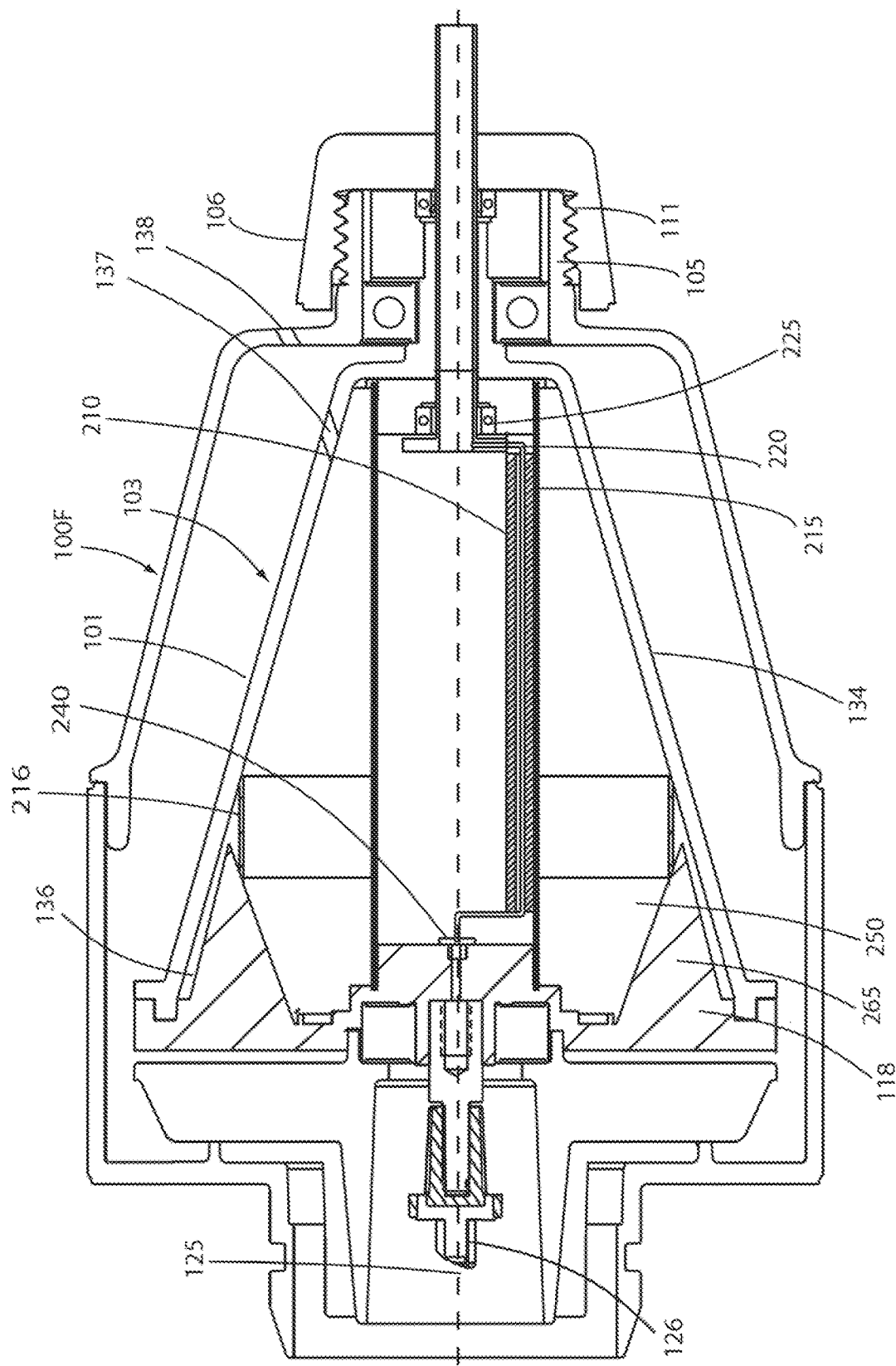
FIG. 7 is a cross section view of still another alternate embodiment of a centrifuge constructed in accordance with this invention making use of a screen element, a roller element, and a secondary screen element.

Another alternative embodiment of a processing unit 100F constructed in accordance with this invention is shown in FIG. 7. The centrifuge using that embodiment is designed to process the tissue material into smaller fragments by morselizing the tissue, by passing the material through a first screen 215, with the aid of roller element 210, as described previously. In this embodiment however, the first screen 215 is configured to morselize the material into smaller fragments, but not to separate the cells from the structure of the tissue material, so as to ensure that the cells remain contained within the native structure of the morselized tissue material. In this embodiment, the secondary screen 216 is a smaller band nearer the entrance to the trap 136, and features openings that allow the passage of liquid material, while retaining the cell-containing tissue material. In this manner, any exogenous fluid (e.g., saline, epinephrine, lidocaine, etc.) added for the collection of the tissue material can pass through the second screen 216, and collect in the trap 136, while the cells would remain in the native structure of the tissue material. Once the separation of liquid from tissue is accomplished, the cell-containing tissue material may be removed from the interior of the inner chamber 103, such as by aspiration with a cannula or other hollow luminal instrument directed through ports 138 and 137. Where the cell containing tissue material has had the majority of the fluids removed by the secondary screen 216, and as such, is not suitable for aspiration as described above, it is contemplated that the operator may simply open the device, using techniques which would be known to those skilled in the art, in order to access the interior of the inner chamber 103, and manually collect the cell-containing tissue material.

As should be appreciated by those skilled in the art the embodiment of FIG. 7 should be useful where a particular clinical application warrants the addition of a scaffold, such as where it is necessary to provide a bulking agent to a treatment site (e.g., plastic surgery, cosmetic wrinkle reduction, etc.); or alternatively in procedures where it is desirable to avoid washing away the harvested cells, for example in arthroscopic surgery where saline irrigation is commonly utilized, and maintaining the delivered cells at the desired site would be beneficial.

Figure 8:
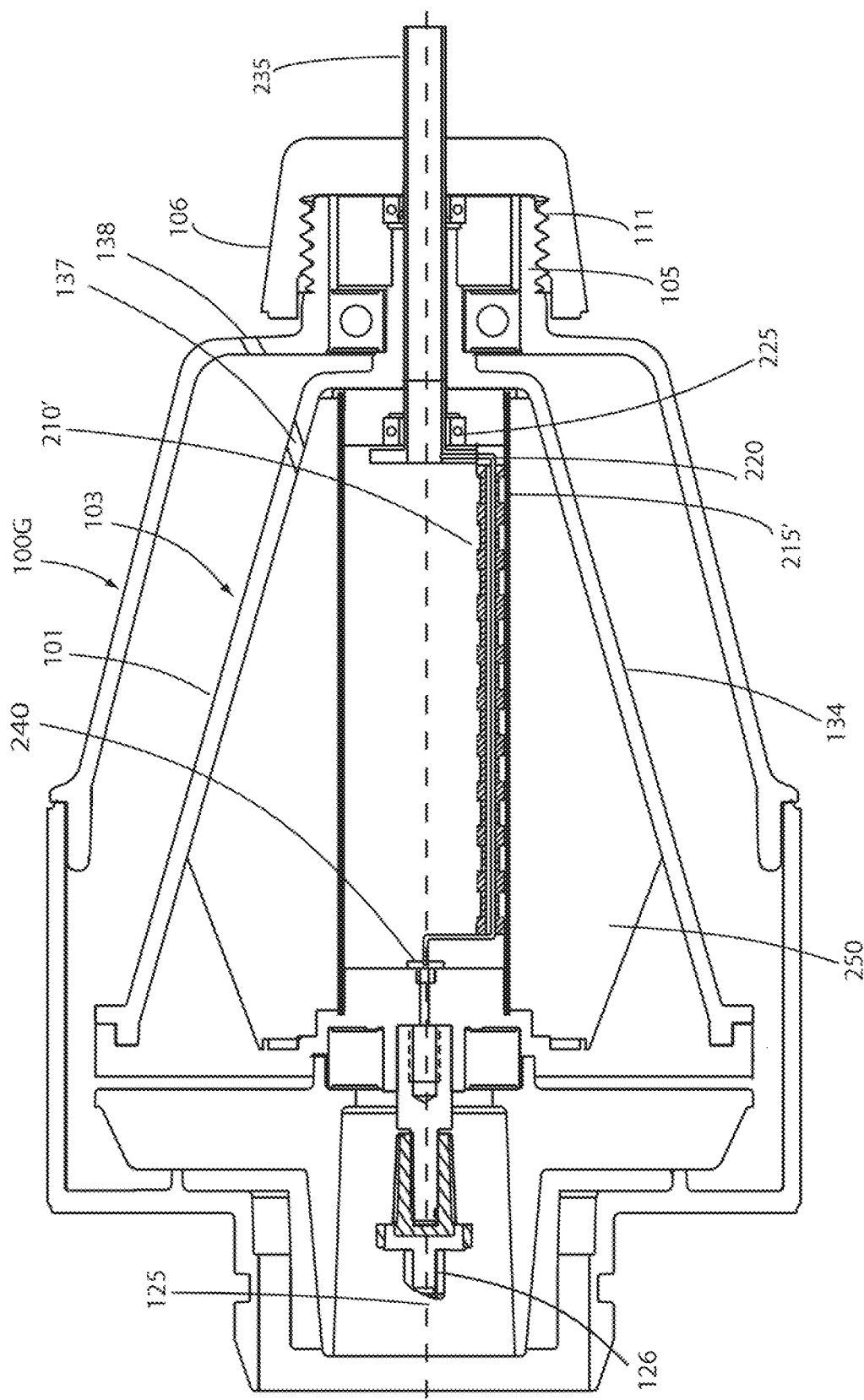
FIG. 8, is a cross-section view of still another alternate embodiment of a centrifuge constructed in accordance with this invention making use of an annular element, and a roller element, with one or more presenting an irregular topography.

Another alternative embodiment of a processing unit 100G constructed in accordance with this invention is shown in FIG. 8. The centrifuge of that embodiment is designed to process the tissue material into smaller fragments by morselizing the tissue, where the tissue material is passed between a roller element 210' arranged to roll in place against a rotating annular element 215', in a manner as has been described previously. It is envisioned that the annular element 215' may be a mesh screen material, as previously described, or may alternatively feature an impermeable surface. Preferably, either one, or both, of the surface of the roller 210', or the surface of the annular element 215' features an irregular topography. This may be accomplished by providing recessed regions and protruding areas on the surface of the cylindrical roller 210'. For example, by providing at least one recessed channel, and leaving protruding areas between the channels, and thus presenting a surface similar to the surface of a waffle iron. Alternatively, the irregular topography of either roller 210' or annular element 215' may feature protruding nubs or bumps, or recessed dimples. What is sought is for the tissue, as it is squeezed between the roller element 210' and the annular element 215', to experience higher degrees of disruption due to the protruding surfaces, and thereby creating concentrated sheer forces in some of the tissue as it passes by the roller. It is believed these sheer forces will provide a morselized slurry, in which the multipotent cells are freed from the containment of the fibrous material. In these embodiments, it is envisioned that all of the tissue material that has been processed would then be collected and utilized in a clinical application, for example as a bulking agent delivered to a treatment site, or in procedures where it is desirable to avoid washing away the harvested cells, as has been described previously with regard to FIG. 7. Where the annular element 215' is a mesh screen, the morselized tissue would be collected from the dished area 250, via the access pathway established through ports 137 and 138, as has been described previously. However, where the annular element 215' is a non-permeable surface, the morselized tissue would remain within the interior of the annular element 215' after processing, and may then be collected with a cannula or needle inserted through the stationary tube.

Figure 9A:
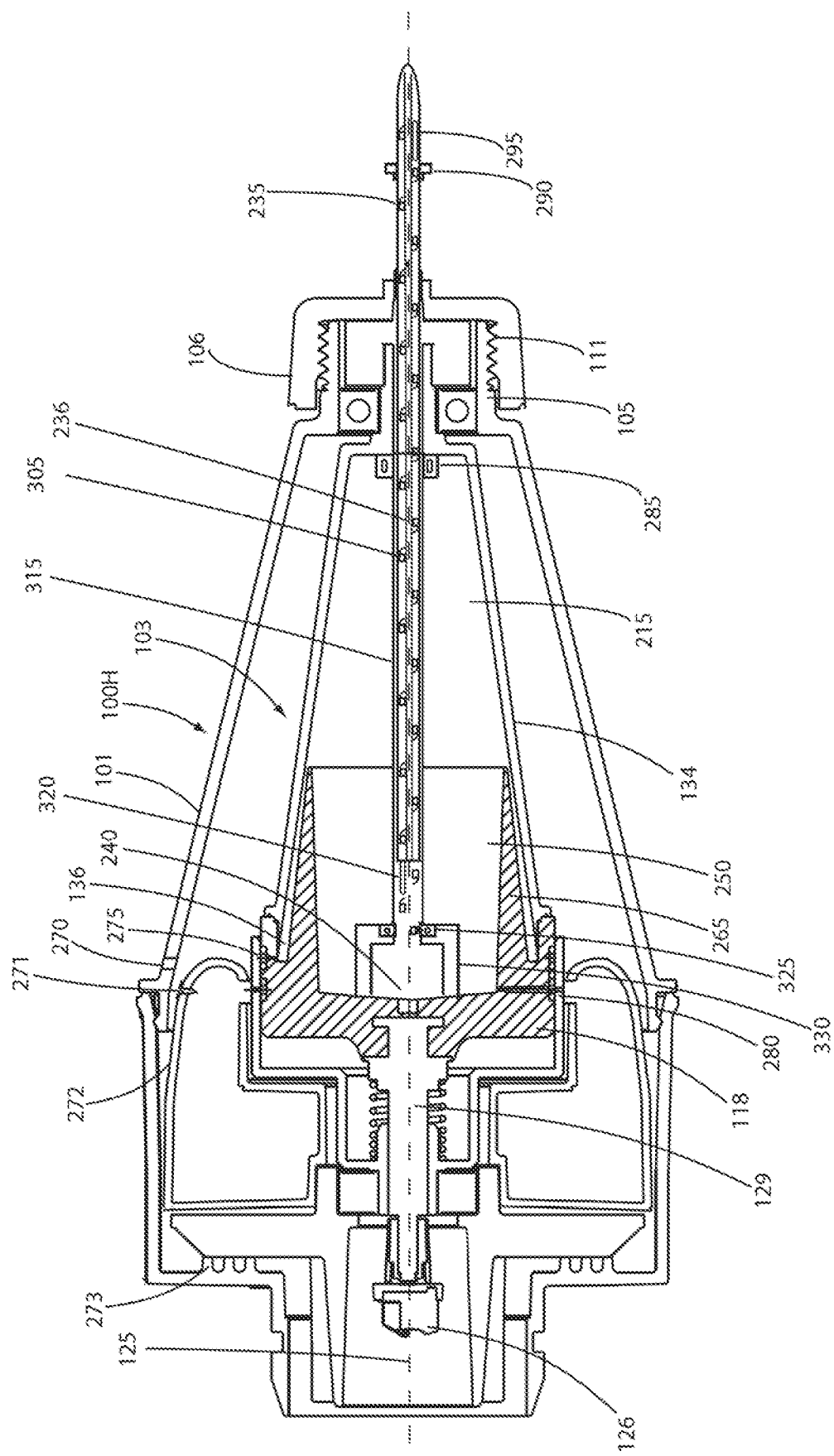
FIG. 9A is a cross section view of another alternative embodiment of a processing unit of a centrifuge constructed in accordance with this invention, wherein the processing unit includes a delivery tube and rotatable sizing helix.

Another alternative embodiment of a processing unit 100H constructed in accordance with this invention is shown in FIG. 9A. The centrifuge using that embodiment is designed to process the tissue material into smaller fragments by first sizing the tissue, by passing the charge of material through a stationary tube 235, containing a sizing helix 305 that is rotatable around a non-rotating core wire 236. The core wire is affixed to the end of the stationary tube. Stationary tube 235, extends into the rotatable chamber 103 and into the rotatable tube 315. In this embodiment, the stationary tube 235 is temporarily fixed to end-cap 106, through techniques known to those skilled in the art. For example, a split ring clamp may be incorporated into the collar of the end cap, where the stationary tube 235 passes through end-cap, such that the clamp may releasably secure the stationary tube relative to the end-cap. The biologic mixture, for example, a charge of fat material, may then be directed through entry port 295, and passed through the interior of the stationary tube to exit through delivery port 320, to enter into the chamber. An optional fitting 290 (e.g. luer connector) may be provided near the top of the stationary tube, so as to securely connect the delivery tube to the container (not shown), typically a syringe, containing the biologic mixture to be processed. The biologic mixture is introduced via a vessel at least temporarily attached to fitting 290, for example by advancing a plunger of a syringe, propelling the biologic mixture through entry port 295 and into the interior of the stationary tube 235 while the sizing helix 305 is rotating. The edge of the entry port 295 may be sharpened to form a cutting edge, such that the rotation of the sizing helix may sever the tissue in the biologic mixture against the cutting edge of the entry port, and further, the rotation of the sizing helix 305 within the stationary tube 235 serves to reduce the particle size of the biologic mixture to a desired range. In the case of the tissue material, the rotating action of the helix within the stationary tube serves to sever the tissue into smaller fragments to create a homogenous material, and further sizes the tissue to a desirable particle size, as the tissue is urged through the interior of the stationary tube to reach the interior of the rotatable chamber 103. The material that is processed through stationary tube 235 by the sizing helix 305 is observed to be a homogenous slurry, having been sized to a consistency suitable for narrow gauge needles used in cosmetic applications, and is anticipated to be suitable for use in fat transfer applications. It is Applicants belief that the ideal particle size of the morselized tissue for re-implanting would lead to better viability of the implanted tissue as the size is such surface area:volume ration for the particles would be conducive revascularization of the implanted tissue and further provide adequate nutrient flow to support cellular growth throughout the entirety of the implanted tissue.

Due to the unique methods of morselizing the tissue, as described herein, whether by operation of the helix within the stationary tube, or by passing the tissue material through a mesh screen element, the tissue material that is processed is anticipated to be reduced to a suitable particle size for re-implantation, but is not anticipated to cause damage to cellular components and the tissue structure, such as may occur by over-processing the tissue to a particle size that is too small. It is anticipated that by providing a tissue that is processed to an appropriate particle size, the material will have preserved cellular viability, while maintaining adequate tissue structure so as to not be susceptible to washout or significant volume loss once implanted.

In all of the embodiments having a sizing helix 305, it is contemplated that the drive unit 20, as shown in FIG. 2, may be attached via coupling 126, which is to effect the rotation of the rotatable chamber 103. In turn, the rotating chamber, when rotating in one direction, will drive the rotation of the sizing helix 305, when the drive unit 20 is activated. With reference to the enlarged view of FIG. 9B, the sizing helix 305 is coupled to the rotatable tube 315 as follows. The rotatable tube 315 is affixed to an insert 310, which is affixed to the end of sizing helix 305 at connection 335, which may be in the form of a solder, weld, or epoxy joint, or other fixing technique known in the art. The rotation of rotatable tube 315 will drive the rotation of the sizing helix through the connection 335 depicted in FIG. 9B.

Figure 9B:
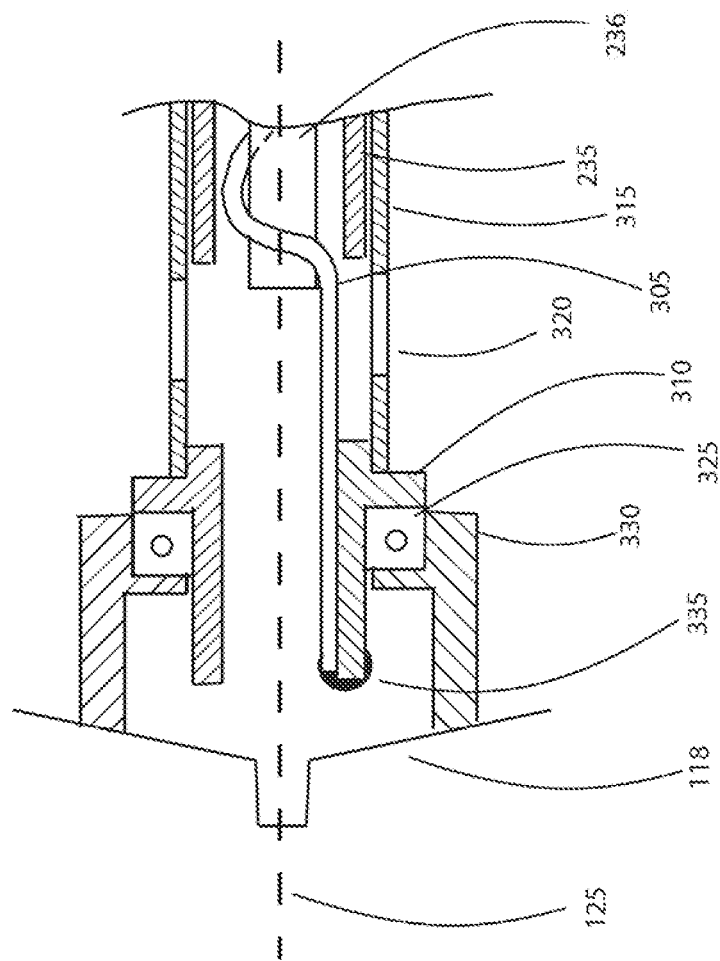
FIG. 9B is an enlarged cross-section view of the embodiment of FIG. 9A, depicting the end of the sizing helix located within the processing unit.

Referring back to FIG. 9A, the rotatable tube 315 is arranged to rotate in concert with the rotatable chamber 103 when rotated in one direction only, through a one-way clutch and roller bearing 285 located between the rotatable tube 315 and the upper end of the rotatable chamber 103. This one way clutch and roller bearing will lock up when rotation force is applied in a first direction, thus transmitting the rotation force from the chamber 103 to the rotatable tube 315 to drive the sizing helix 305. However, when the rotatable chamber is rotated in the second (opposite) direction, the one way roller clutch and roller bearing 285 will freewheel, and serves to isolate the rotation of the chamber 103 from the rotatable tube 315, thus the sizing helix will then remain stationary as the rotatable chamber is rotating. As can be seen in FIG. 9B, a platform bearing 325 which is located between the insert 310 and the platform 330 will isolate stationary rotatable tube 315 only when the rotatable chamber 103 is rotating in the second direction. The legs of the platform 330 are attached to the base 118, and the platform thus rotates with the rotatable chamber 103. The platform 330 provides openings between the platform legs, so as to allow fluid flow under the platform, and may be similar to a 3-legged stool.

For all of the embodiments having a sizing helix 305, while in use, the biologic mixture is to be introduced into the device while the chamber 103, the sizing helix 305 and rotatable tube 315 are rotating in a first direction. The biologic mixture passes through the stationary tube 235, while the sizing helix is rotating about the core wire 236, within the stationary tube, and thus serves to whisk the biologic mixture, and sizes the biologic mixture to a desirable particle size that is smaller than the initial average particle size of the biologic mixture, prior to being placed in the device. Once the entire sample of the biologic mixture to be processed is within the chamber 103, the direction of rotation may then be reversed, thereby halting the rotation of the sizing helix 305, and the chamber 103 can then rotated to effect the separation of the biologic mixture by specific gravity, as has been discussed previously.

As can be seen in the exemplary embodiment of FIG. 9A, the biologic mixture is introduced to the chamber 103 through the stationary tube 235. The chamber is then rotated to separate the biologic mixture by specific gravity, as has been described previously. In the case where the biologic mixture comprises at least fat tissue, blood and optionally saline, water, tumescent solution, upon separation of the biologic mixture, the red blood cells, having the highest specific gravity would accumulate at the outermost layer, while the fat, plasma and water, if any, would accumulate at the innermost layer, having the lowest specific gravity. At least a portion of the outermost fraction, e.g. red blood cells, may be discharged by opening the valving for first port 275, then closing the first port after an appropriate amount of the first fraction have been ejected, as determined by observing the color interface between the red blood cells and the fraction with the multipotent stem cells. The operator is able to monitor the location of the interface through a transparent sidewall, so as to allow the operator to close the valve as the interface nears the outlet for the red blood cells. Subsequently, at least a portion of the innermost fraction, e.g., plasma and fat, and any water or tumescent fluid, may be ejected by opening the valving for the second port 280, and closing the second port after the air core has reached the second port. The rotation may then be halted, whereupon the portion of the biologic mixture remaining within the chamber will pool at bottom of the chamber, and can be removed by inserting a cannula into the chamber. This fraction remaining will largely consist of the multipotent stem cells and platelet rich plasma.

Figure 10:
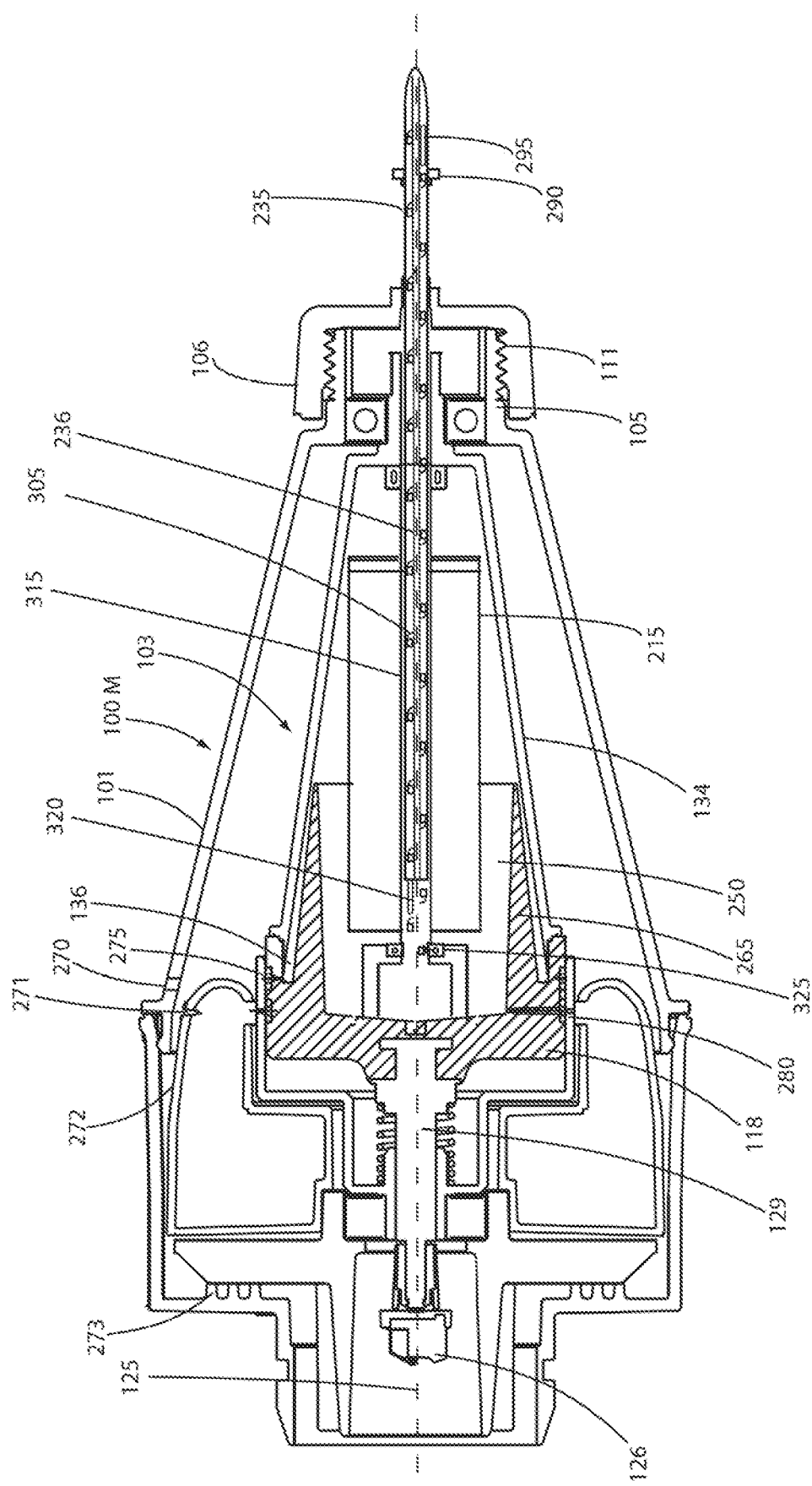
FIG. 10 is a cross section view of another alternative embodiment of a processing unit of a centrifuge constructed in accordance with this invention, wherein the processing unit includes a screen element, a delivery tube and rotatable sizing helix.

Another alternative embodiment of a processing unit 100M constructed in accordance with this invention is shown in FIG. 10. The embodiment in FIG. 10 is similar to that depicted in FIG. 9, with the distinction of providing an annular screen element 215, located within the inner chamber 103 and extending concentrically around the central longitudinal axis 125 (i.e., the axis of rotation). The biologic mixture may be sized by passing through the sizing helix as described previously. However, once the sized material exits the rotatable tube 315 through delivery port 320, it will be within an annular screen element 215. The screen element 215 is affixed at each end to the rotatable tube 315, so that material passing from a region within the annulus of screen element 215 to the outside of the screen element must necessarily pass through the openings provided in the screen element. The screen element is a mesh-like member that may be a metal or polymer wire material, or alternatively a perforated sheet providing openings sized to pass fluid material, but retain much of the fibrous material. It is envisioned that the openings will be uniformly or non-uniformly sized between 0.002 and 0.040 inches. Thus the screen element 215 may serve to further size the biologic mixture material, and may further serve as a sieve, to capture fibrous elements from the disrupted tissue.

As can be seen in the exemplary embodiment of FIG. 10, the biologic mixture is to be introduced to the chamber 103 by passing through the stationary tube 235 where it is sized by the sizing helix 305, as previously discussed. The chamber rotation may then be reversed to halt the helix rotation, and to cause the material to pass through the screen element 215. Subsequently, continued rotation of the chamber will separate the biologic mixture by specific gravity, as has been described previously. In the case where the biologic mixture comprises at least fat tissue, blood and optionally saline, water, tumescent solution, upon separation of the biologic mixture by specific gravity, the red blood cells, having the highest specific gravity would accumulate at the outermost layer, while the fat, plasma and water, if any, would accumulate at the innermost layer, having the lowest specific gravity. At least a portion of the outermost fraction, e.g. red blood cells, may be discharged by opening the valving for first port 275, then closing the first port after an appropriate amount of the first fraction have been ejected, as determined by observing the color interface between the red blood cells and the fraction with the multipotent stem cells. The operator is able to monitor the location of the interface through a transparent sidewall, so as to allow the operator to close the valve as the interface nears the outlet for the red blood cells. Subsequently, at least a portion of the innermost fraction, e.g., plasma and fat, may be ejected by opening the valving for the second port 280, and closing the second port after the air core has reached the second port. The rotation may then be halted, whereupon the portion of the biologic mixture remaining within the chamber will pool at bottom of the chamber, and can be removed by inserting a cannula into the chamber. This fraction remaining will largely consist of the multipotent stem cells and platelet rich plasma.

Figure 11:
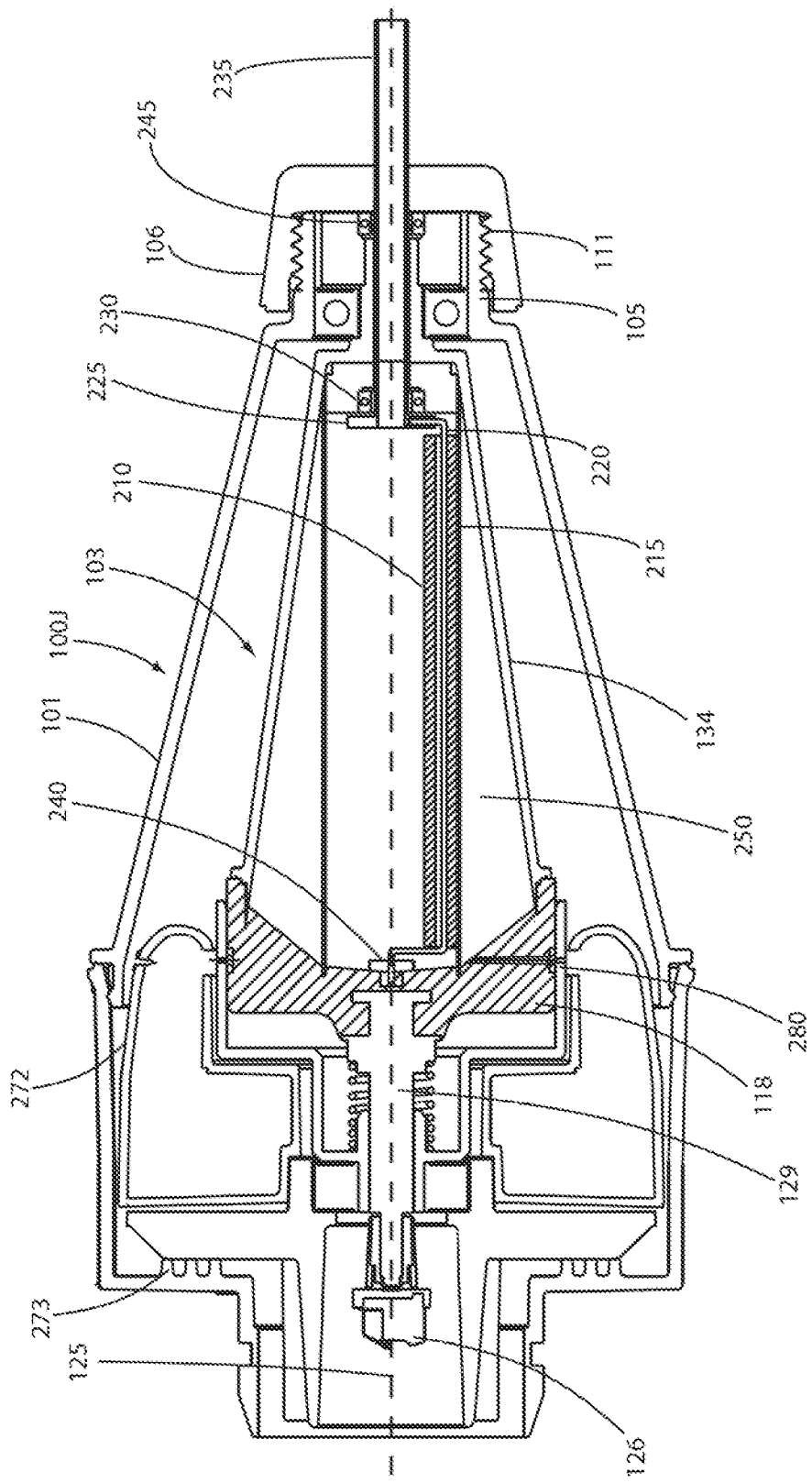
FIG. 11 is an enlarged cross section view of still another alternate embodiment of a processing unit of a centrifuge with a screen element and roller element constructed in accordance with this invention.

Another alternative embodiment of a processing unit 100J constructed in accordance with this invention is shown in FIG. 11. The embodiment in FIG. 11 is similar to that depicted in FIG. 4, with the distinction that following elements from FIG. 4 are absent from FIG. 11: wedge 265, trap 136, first port 275. Additionally, the base 118 now extends directly to the inner surface of the sidewall 134, in a taper, rather than form a wedge element.

As can be seen in the exemplary embodiment of FIG. 11, the biologic mixture is to be introduced to the chamber 103 and sized by passing through the screen element 215, as described with reference to FIG. 4. Upon rotation of the chamber 103, the material will be urged through screen element 215 by roller element 210, as described previously. The act of passing through the screen may disrupt the structure of the tissue material, so as to release the multipotent stem cells from the structure. Continued rotation of the chamber 103 will cause the separation of the biologic mixture by specific gravity, as has been described previously. In the case where the biologic mixture comprises fat and water or tumescent solution, upon separation, the multipotent stem cells having a higher specific gravity than the fat or the water, will accumulate at the outermost layer within the rotating chamber. At least a portion of the innermost fraction may be discharged by opening the valving for the port 280. It is contemplated that the fat and water components would then be discharged from the chamber 103 through port 280, until the air core encounters the entrance to port 280, and halting the discharge. It is contemplated that the fraction of the biologic mixture remaining within the chamber would include the multipotent stem cells, now having been concentrated by removal of fat and water from the biologic mixture. Upon halting the rotation of the chamber, the remaining fraction will pool in the center of the chamber for collection.

Figure 12:
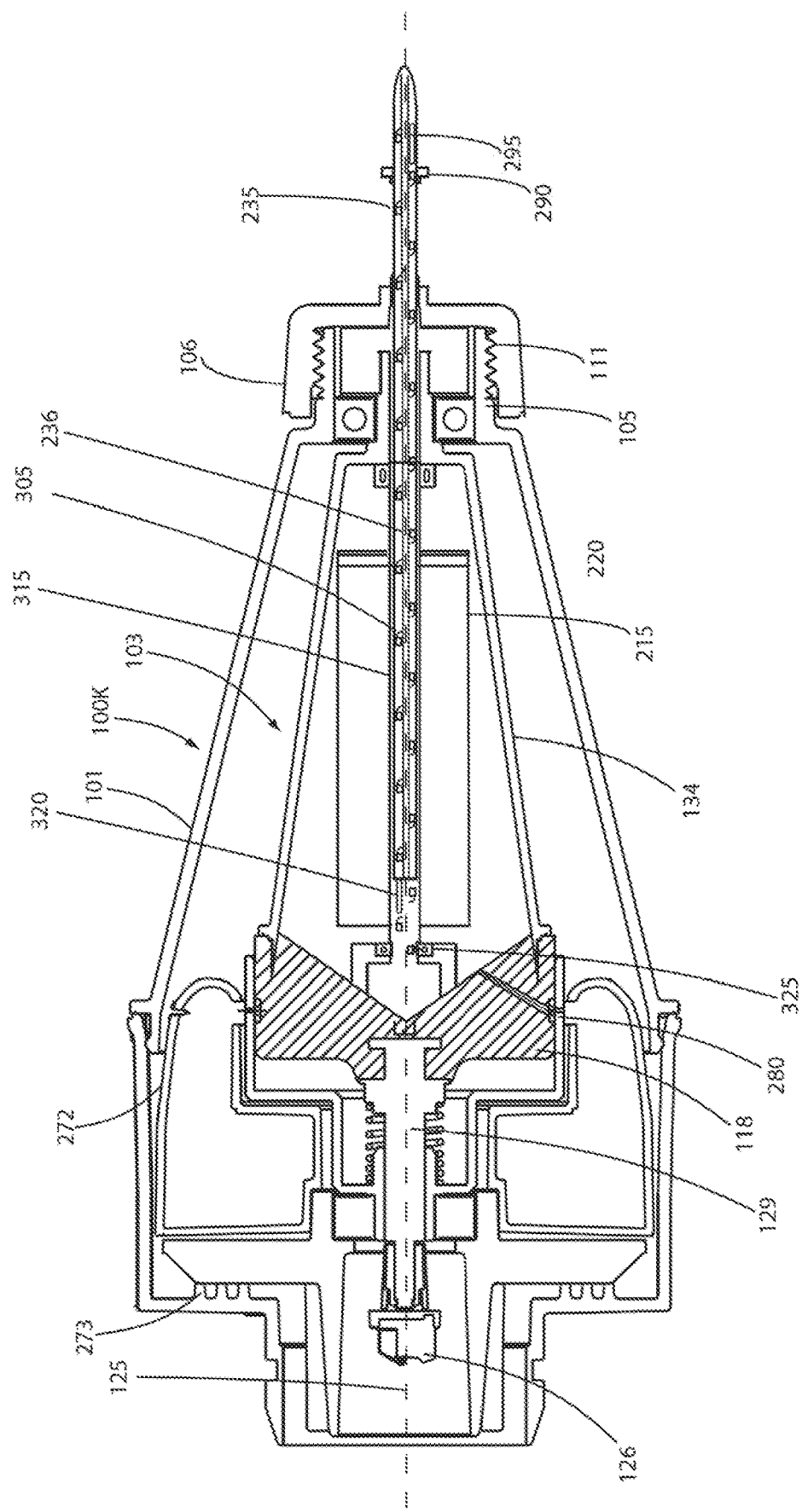
FIG. 12 is a cross-section view of still another alternative embodiment of a processing unit of a centrifuge constructed in accordance with this invention, wherein the processing unit includes a screen element, a delivery tube and rotatable sizing helix.

Another alternative embodiment of a processing unit 100K constructed in accordance with this invention is shown in FIG. 12. The embodiment in FIG. 12 is similar to that depicted in FIG. 10, with the distinction that following elements from FIG. 10 are absent from FIG. 12: wedge 265, trap 136, first port 275. Additionally, the base 118 now extends directly to the inner surface of the sidewall 134, in a taper, rather than form a wedge element.

As can be seen in the exemplary embodiment of FIG. 12, the biologic mixture is to be introduced to the chamber 103 by passing through the stationary tube 235 where it is sized by the sizing helix 305, as previously discussed. The chamber rotation may then be reversed to halt the helix rotation, and to cause the material to pass through the screen element 215 as previously described. Subsequently, continued rotation of the chamber will separate the biologic mixture by specific gravity, as has been described previously. In the case where the biologic mixture comprises fat and water or tumescent solution, upon separation, the multipotent stem cells having a higher specific gravity than the fat or the water, will accumulate at the outermost layer within the rotating chamber. At least a portion of the innermost fraction may be discharged by opening the valving for the port 280. It is contemplated that the fat and water components, having the lowest specific gravities, would then be discharged from the chamber 103 through port 280, until the air core encounters the entrance to port 280, and halting the discharge. It is contemplated that the fraction of the biologic mixture remaining within the chamber would include the multipotent stem cells, now having been concentrated by removal of fat and water from the biologic mixture. Upon halting the rotation of the chamber, the remaining fraction will pool in the center of the chamber for collection.

Figure 13:
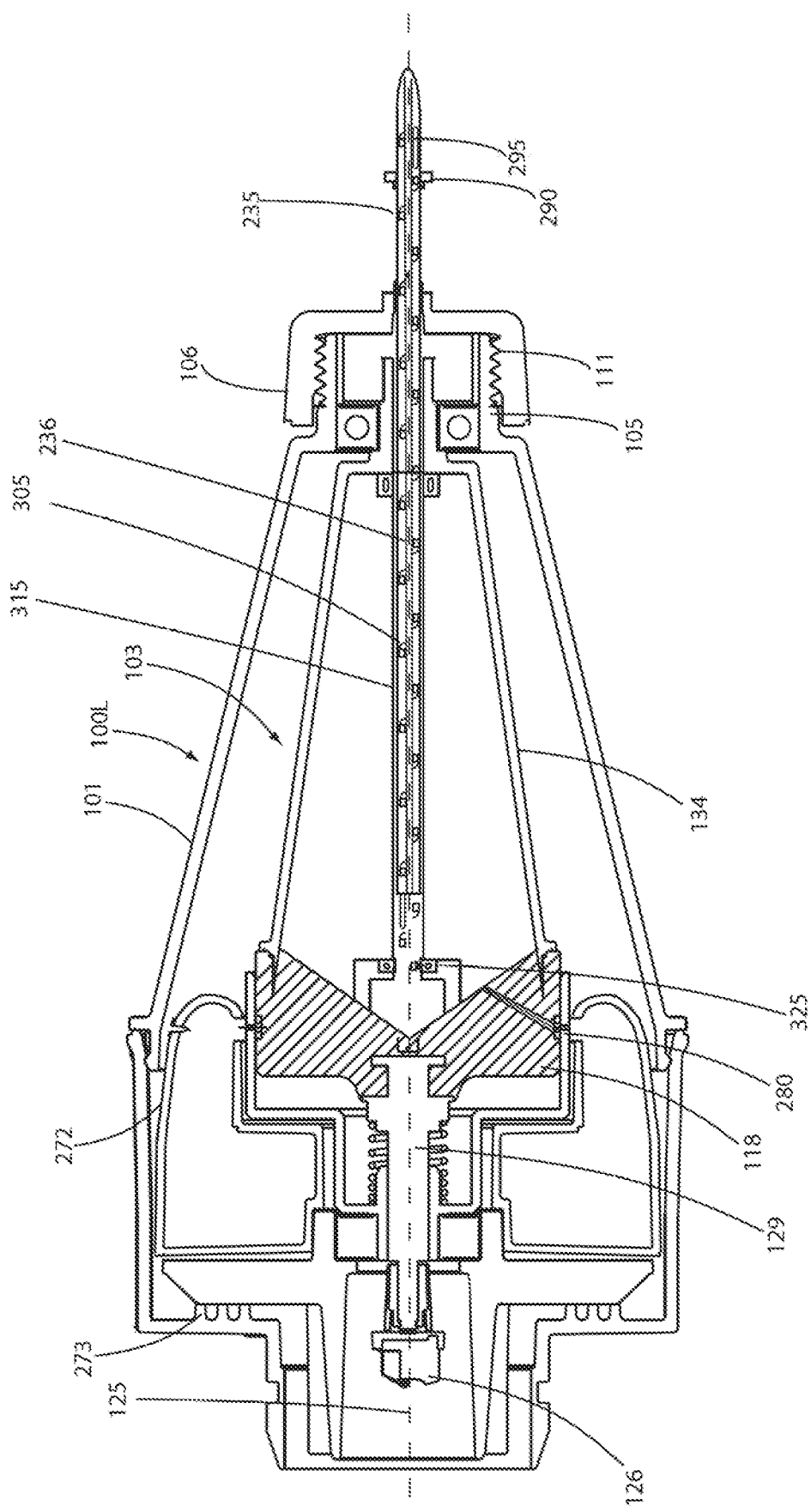
FIG. 13 is a cross section view of still another alternative embodiment of a processing unit of a centrifuge constructed in accordance with this invention, wherein the processing unit includes a delivery tube and rotatable sizing helix.

Another alternative embodiment of a processing unit 100L constructed in accordance with this invention is shown in FIG. 13. The embodiment in FIG. 13 is similar to that depicted in FIG. 12, with the distinction that the embodiment of FIG. 13 lacks the annular screen element of FIG. 12. As with FIG. 12, the base 118 now extends directly to the inner surface of the sidewall 134, in a taper, rather than form a wedge element.

As can be seen in the exemplary embodiment of FIG. 13, the biologic mixture is to be introduced to the chamber 103 by passing through the stationary tube 235 where it is sized by the sizing helix 305, as previously discussed. The chamber rotation may then be reversed to halt the helix rotation. Continued rotation of the chamber will separate the biologic mixture by specific gravity, as has been described previously. In the case where the biologic mixture comprises fat and water or tumescent solution, upon separation, the multipotent stem cells, having a higher specific gravity than the fat or the water, will accumulate at the outermost layer within the rotating chamber. At least a portion of the innermost fraction may be discharged by opening the valving for the port 280. It is contemplated that the fat and water components, having the lowest specific gravities, would then be discharged from the chamber 103 through port 280, until the air core encounters the entrance to port 280, and halting the discharge. It is contemplated that the fraction of the biologic mixture remaining within the chamber would include the multipotent stem cells, now having been concentrated by removal of fat and water from the biologic mixture. Upon halting the rotation of the chamber, the remaining fraction will pool in the center of the chamber for collection.

It should be pointed out at this juncture that any of the above described exemplary embodiments (or any other embodiments constructed in accordance with the teachings of this invention) will produce a concentrated cell fraction that may be usefully combined with (e.g., hydrated into, mixed with, kneaded into, provided as a depot within, or layered onto) a synthetic or natural scaffold or structure which may be implanted into a treatment site of a living being. Such combining of the cell fraction with the scaffold may be accomplished in various manners, for example, by hydrating the scaffold with the cellular fraction, mixing the cell fraction with scaffold material, kneading the scaffold material and cell fraction together, providing the cell fraction as a depot contained within the scaffold material, coating the scaffold with the cell fraction, applying the cell fraction as a layer alongside a scaffold material, sequentially adding the cell fraction to a target site followed by placement of a scaffold material to the target site, or vice versa. Various other procedures for combining a scaffold with a cell fraction may be well known to those skilled in the art and may be suitable for use with the cell fraction created as described herein.

Moreover, while the previously described embodiments have focused on the concentration of multi-potent cells, in any of the embodiments, it is recognized that various cells along with, or instead of, the multipotent cells may be concentrated, which may include adipocytes, as well as the stromal vascular fraction (SVF) of cells including preadipocytes, fibroblasts, vascular endothelial cells and a variety of immune cells (e.g., adipose tissue macrophages, etc.). It is contemplated that by manipulating the location of the outlet ports 275 and 280, the range of specific gravities to be collected can be controlled, such that all of the sample, or just a select portion of the cellular components in the sample can be isolated through the use of the various embodiments described herein.

The above described embodiments may be made available in kit form, including the centrifuge device and accessories needed for operation of the device, including instructions for use and packaging suitable for storage and preserving sterility. In some instances, the kit may provide instructions along with the centrifuge device (either as a single unit, or separable components), and optionally including accessories such as any or all of needles, syringes, cannulas, lidocaine, epinephrine, tumescent solution, liposuction kits and instructions for use.

As should be appreciated by those skilled in the art from the foregoing the apparatus and methods of this invention can be used to provide an injectable concentrate having a larger quantity of multipotent cells that is comparable or better than bone marrow concentrated aspirate of the same volume without requiring the need for a painful iliac crest puncture to harvest cells therefrom. In addition, the subject invention enables one to reduce the time of the procurement process of a usable multipotent cell sample, to a few minutes, so as to allow the use of the equipment in the operatory ad-hoc, if so required. Further still the subject invention eliminates the need for the use of enzymes or chemicals to be added to the sample for processing, yet which would need to be washed from the sample, prior to being injected back into the patient. Thus, the subject invention overcomes the inefficiencies of enzymatic treatments, which typically lead to lower cellular yields.

For any of the above described embodiments, it is contemplated to optionally include a heating source, in order to maintain the biologic mixture at a temperature above ambient temperature. This may be useful where the biologic mixture includes adipose tissue, and the increase in temperature, preferably to body temperature (37 C) would serve to reduce the viscosity of the adipose tissue. In this manner, when the tissue is processed, cell viability may be improved as the cells, e.g., multipotent stem cells, would be exposed to lower levels of shear stress during processing. In contrast, where the processing is performed at a lower temperature, the viscosity of the adipose tissue would increase, and potentially harming cell viability due to the increase in shear stress that would occur when processed by any of the embodiments described herein.

Thus since the inventive process and inventions disclosed herein may be embodied by additional steps or other specific forms without departing from the spirit of general characteristics thereof, some of which steps and forms have been indicated, the embodiments described herein are to be considered in all respects illustrative and not restrictive. The scope of the invention is to be indicated by the appended claims, rather than the foregoing description, and all changes which come within the meaning and range of equivalency of the claims are intended to be embraced therein.

What is claimed is:

1. A method for processing a biologic mixture and selectively concentrating constituents of the biologic mixture, the constituents having differing specific gravities and being stratifiable in a centrifugal field, said method comprising:
   a. introducing a biologic mixture comprising adipose tissue into a chamber of a centrifuge, said chamber comprising a sidewall with a tapered inner surface, a base, an annular screen having an inner surface, and a first port; and
   b. rotating said chamber about an axis to pass at least a substantial portion of said adipose tissue through said annular screen, thereby morselizing the substantial portion of said adipose tissue; and causing the biologic mixture to stratify in said chamber into at least two concentric stratified constituent layers.

2. The method of claim 1, wherein the biologic mixture comprises adipose tissue and water based liquids.

3. The method of claim 1, wherein one of the at least two concentric stratified constituent layers comprise multipotent cells.

4. The method of claim 3, further comprising the step of harvesting said multipotent cells from said centrifuge.

5. The method of claim 1, wherein the annular screen has an inner surface located at a first radial distance from the axis, the annular screen projecting away from the base.

6. The method of claim 5, wherein the centrifuge further comprises a roller arranged to roll around the inner surface of the annular screen and urge at least a portion of the biologic mixture through the annular screen and away from the axis and towards the sidewall.

7. The method of claim 5, wherein the centrifuge further comprises a roller arranged to roll against and around the inner surface of the annular screen and urge at least a portion of the biologic mixture through the annular screen and away from the axis and towards the sidewall.

8. The method of claim 1, wherein the centrifuge further comprises a first port having an inlet at a second radial distance from said axis, wherein the first port is selectively openable to allow the discharge of at least a portion of a constituent from the chamber.

9. The method of claim 6, wherein the chamber further comprises at least one roller axle extending parallel to said axis, said roller being arranged to spin about said at least one roller axle to roll around said inner surface of said annular screen.

10. The method of claim 9, wherein said at least one roller axle is held stationery relative to said chamber.

11. The method of claim 7, wherein the chamber further comprises at least one roller axle extending parallel to said axis, said roller being arranged to spin about said at least one roller axle to roll around said inner surface of said annular screen and wherein said at least one roller axle is held stationery relative to said chamber.

12. The method of claim 1, wherein said annular screen is a perforated material selected from the group consisting of wire mesh screen, polymer mesh screen, perforated metal tubing and perforated polymer tubing.

13. The method of claim 1, wherein the chamber further comprises a trap, said trap being located in said chamber adjacent said inner surface of said sidewall, and said chamber, and wherein the centrifuge further comprises at least one port and a valve for selectively ejecting at least a portion of at least one of said constituent layers from the trap.

14. The method of claim 1, wherein the annular screen comprises plural openings in the range of approximately 0.04 inches to approximately 0.002 inches.

15. The method of claim 1, wherein the annular screen rotates at the same speed as the chamber.

16. The method of claim 5, wherein the chamber further comprises a secondary screen, the secondary screen being located at a fifth radial distance from the axis, wherein the fifth radial distance is greater than the first radial distance, wherein the secondary annular screen has a smaller opening size than the annular screen, and wherein the secondary annular screen is configured to capture fibrous material while allowing non-fibrous material and liquid to pass through.

17. The method of claim 6, wherein the chamber further comprises a secondary screen, the secondary screen being located at a fifth radial distance from the axis, wherein the fifth radial distance is greater than the first radial distance, wherein the secondary annular screen has a smaller opening size than the annular screen, and wherein the secondary annular screen is configured to capture fibrous material while allowing non-fibrous material and liquid to pass through.

18. The method of claim 11, wherein the chamber further comprises a secondary screen, the secondary screen being located at a fifth radial distance from the axis, wherein the fifth radial distance is greater than the first radial distance, wherein the secondary annular screen has a smaller opening size than the annular screen, and wherein the secondary annular screen is configured to capture fibrous material while allowing non-fibrous material and liquid to pass through.

19. The method of claim 1, wherein the centrifuge further comprises an end cap on the chamber and a stationary tube that extends through the end cap, wherein the stationary tube is configured for directing said biologic mixture into said chamber and the biologic mixture is introduced into the chamber via the stationary tube.

20. The method of claim 19, wherein the centrifuge further comprises a sizing helix and a core wire, wherein the sizing helix is at least partially contained within said stationary tube and is rotatable about said core wire.

21. The method of claim 1, further comprising the step of:
c. ejecting from the chamber through the first port a higher density portion of the biologic mixture that has passed through the annular screen.

22. The method of claim 21, further comprising the step of:
d. recovering from the chamber a portion of the biologic mixture that has passed through the annular screen and remains within the chamber.

* * * * *